US009597432B2

(12) United States Patent
Nakamura

(10) Patent No.: US 9,597,432 B2
(45) Date of Patent: *Mar. 21, 2017

(54) CELL CONSTRUCT COMPRISING POLYMER BLOCKS HAVING BIOCOMPATIBILITY AND CELLS

(75) Inventor: Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/582,362

(22) PCT Filed: Mar. 1, 2011

(86) PCT No.: PCT/JP2011/054577
§ 371 (c)(1),
(2), (4) Date: Aug. 31, 2012

(87) PCT Pub. No.: WO2011/108517
PCT Pub. Date: Sep. 9, 2011

(65) Prior Publication Data
US 2012/0329157 A1 Dec. 27, 2012

(30) Foreign Application Priority Data

Mar. 1, 2010 (JP) .................. 2010-044023
Oct. 4, 2010 (JP) .................. 2010-224628

(51) Int. Cl.
*C12N 5/00* (2006.01)
*C12N 5/02* (2006.01)
(Continued)

(52) U.S. Cl.
CPC ............. *A61L 27/58* (2013.01); *A61L 27/222* (2013.01); *A61L 27/38* (2013.01); *C12N 5/0068* (2013.01);
(Continued)

(58) Field of Classification Search
None
See application file for complete search history.

(56) References Cited

U.S. PATENT DOCUMENTS 5,876,756 A * 3/1999 Takada et al. ................. 424/489
5,904,717 A * 5/1999 Brekke et al. ................. 424/423
(Continued)

FOREIGN PATENT DOCUMENTS

JP 2003-275294 A 9/2003
JP 2004-267562 A 9/2004
(Continued)

OTHER PUBLICATIONS

Chen et al., Biomater., 27:4453-4460 (2006).*
(Continued)

*Primary Examiner* — Thomas J Visone
(74) *Attorney, Agent, or Firm* — Sughrue Mion, PLLC

(57) ABSTRACT

It is an object of the present invention to provide a cell three-dimensional construct that has a thickness sufficient for tissue regeneration and comprises cells uniformly distributed therein. The present invention provides a cell construct comprising polymer blocks having biocompatibility and cells, wherein the plural polymer blocks are arranged in spaces between the plural cells.

13 Claims, 22 Drawing Sheets
(5 of 22 Drawing Sheet(s) Filed in Color)

(51) Int. Cl.
 A61L 27/58 (2006.01)
 A61L 27/22 (2006.01)
 A61L 27/38 (2006.01)
(52) U.S. Cl.
 CPC ...... C12N 2533/40 (2013.01); C12N 2533/76 (2013.01)

(56) References Cited

U.S. PATENT DOCUMENTS

| | | | |
|---|---|---|---|
| 6,992,172 B1* | 1/2006 | Chang et al. | 530/354 |
| 8,101,205 B2* | 1/2012 | Bouwstra et al. | 424/469 |
| 8,158,756 B2* | 4/2012 | De Boer et al. | 530/356 |
| 8,198,086 B2 | 6/2012 | Koga et al. | |
| 2003/0064074 A1* | 4/2003 | Chang et al. | 424/184.1 |
| 2005/0229264 A1* | 10/2005 | Chang et al. | 800/8 |
| 2006/0088569 A1 | 4/2006 | Kawata et al. | |
| 2008/0220521 A1 | 9/2008 | Kawata et al. | |
| 2009/0035349 A1* | 2/2009 | Gazit et al. | 424/423 |
| 2009/0098177 A1 | 4/2009 | Werkmeister et al. | |
| 2009/0143568 A1* | 6/2009 | Chang et al. | 530/354 |
| 2009/0228027 A1 | 9/2009 | Yamanaka et al. | |
| 2009/0246282 A1 | 10/2009 | Kluijtmans et al. | |
| 2010/0048481 A1* | 2/2010 | Bouwstra et al. | 514/12 |
| 2010/0075902 A1* | 3/2010 | De Boer et al. | 514/12 |
| 2010/0093053 A1* | 4/2010 | Oh et al. | 435/176 |
| 2010/0119574 A1* | 5/2010 | De Boer et al. | 424/423 |
| 2010/0158982 A1 | 6/2010 | Kawata et al. | |
| 2011/0200559 A1 | 8/2011 | Koga et al. | |
| 2012/0156132 A1* | 6/2012 | Nakamura et al. | 424/1.69 |
| 2012/0165263 A1* | 6/2012 | Hiratsuka et al. | 514/16.9 |
| 2012/0195828 A1* | 8/2012 | Nakamura et al. | 424/1.11 |
| 2012/0196807 A1* | 8/2012 | Nakamura et al. | 514/15.4 |

FOREIGN PATENT DOCUMENTS

| | | |
|---|---|---|
| JP | 2006-116212 A | 5/2006 |
| JP | 2008-228744 A | 10/2008 |
| JP | 2009-112233 A | 5/2009 |
| JP | 2009-520501 A | 5/2009 |
| JP | 2009-240766 A | 10/2009 |
| WO | 2007/073190 A1 | 6/2007 |
| WO | 2008/103041 A1 | 8/2008 |
| WO | WO 2008/103041 * 8/2008 | ............ C07K 14/78 |
| WO | WO 2008/103042 * 8/2008 | ............ C07K 14/78 |
| WO | 2008123614 | 10/2008 |
| WO | WO 2009/002456 * 12/2008 | ............ C12N 5/08 |
| WO | 2009/066468 A1 | 5/2009 |
| WO | 2009106642 A1 | 9/2009 |
| WO | 2010/110067 A1 | 9/2010 |

OTHER PUBLICATIONS

Goetghebeur et al., App. Microbiol. Biotechnol., 34:735-741 (1991).*
Kim et al., J. Controlled Rel., 91(3):654-374 (2003).*
Lao et al., Collids Surf. B: Biointer., 66(2):218-225 (2008).*
Malafaya et al., J. Mater. Sci., 16:1077-1085 (2005).*
Malda et al., Trends. Biotechnol., 24(7):299-304 (2006).*
Park et al., Biomater., 28(21):3217-3227 (2007).*
Goetghebeur et al., Appl. Microbiol. Biotechnol., 34:735-741 (1991).*
Curcio et al., Biomater., 28:5487-5497 (2007).*
Glicklis et al., Biotech. Bioeng., 86(6):672-680 (2004).*
Friedrich et al. J. Biomol. Screening, 12(7):925-937 (2007).*
Carlsson et al., Recent Results in Cancer Research, pp. 1-12 (1984).*
Botchwey et al., J. Biomed. Mater. Res., 67A:357-367 (2003).*
Haji-Karim et al., Cancer Res., 38:1457-1464 (1978).*
Mei et al., J. Biotechnol., 150:438-446 (2010).*
Mueller-Klieser et al., 53:345-353 (1986).*
Translation of International Preliminary Report on Patentability dated Sep. 20, 2012 in International Application No. PCT/JP2011/054577.
International Preliminary Report on Patentability dated Sep. 13, 2012 in International Application No. PCT/JP2011/054577.
Masami Harimoto et al., "Novel approach for achieving double-layered cell sheets co-culture: overlaying endothelial cell sheets onto monolayer hepatocytes utilizing temperature-responsive culture dishes", J. Biomed. Mater. Res., 2002, pp. 464-470, vol. 62.
Tatsuya Shimizu et al., "Cell sheet engineering for myocardial tissue reconstruction", Biomaterials, 2003, pp. 2309-2316, vol. 24.
Teruo Okano, The 26th annual meeting of the Japanese Society of Inflammation and Regeneration-Pursuing fusion between inflammation research and regenerative medicine, Inflammation and Regeneration, 2005, pp. 158-159, vol. 25, No. 3.
Jason Yang et al., "Sustained growth and three-dimensional organization of primary mammary tumor epithelial cells embedded in collagen gels", Proc. Natl. Acad. Sci., 1979, pp. 3401-3405, vol. 76, No. 7.
Tatsuya Shimizu et al., "Fabrication of Pulsatile Cardiac Tissue Grafts Using a Novel 3-Dimensional Cell Sheet Manipulation Technique and Temperature-Responsive Cell Culture Surfaces", Circ. Res., 2002, pp. 40-48, vol. 90.
Al Kushida et al., "Temperature-responsive culture dishes allow nonenzymatic harvest of differentiated Madin-Darby canine kidney (MDCK) cell sheets", J. Biomed. Mater. Res., 2000, pp. 216-223, vol. 51.
Al Kushida et al., "Decrease in culture temperature releases monolayer endothelial cell sheets together with deposited fibronectin matrix from temperature-responsive culture surfaces", J. Biomed. Mater. Res., 1999, pp. 355-362, vol. 45.
Tatsuya Shimizu et al., "Two-Dimensional Manipulation of Cardian Myocyte Sheets Utilizing Temperature-Responsive Culture Dishes Augments the Pulsatile Amplitude", Tissue Engineering, 2001, pp. 141-151, vol. 7, No. 2.
Tatsuya Shimizu et al., "Electrically communicating three-dimensional cardiac tissue mimic fabricated by layered cultured cardiomyocyte sheets", J. Biomed. Mater. Res., 2002, pp. 110-117, vol. 60.
Lihong Lao et al., "Chitosan modified poly(L-lactide) microspheres as cell microcarriers for cartilage tissue engineering", Colloids and Surfaces B: Biointerfaces, 2008, pp. 218-225, vol. 66.
Ying-Nan Wu et al., "Cartilaginous ECM component-modification of the micro-bead culture system for chondrogenic differentiation of mesenchymal stem cells", Biomaterials, 2007, pp. 4056-4067, vol. 28.
Hyun Jung Chung et al., "Injectable Cellular Aggregates Prepared from Biodegradable Porous Microspheres for Adipose Tissue Engineering", Tissue Engineering, 2009, pp. 1391-1400, vol. 15, No. 6.
I. Gercek et al., "A novel scaffold based on formation and agglomeration of PCL microbeads by freeze-drying", J. of Biomat. Res. Part A, 2008, pp. 1012-1022, vol. 86.
International Search Report for PCT/JP2011/054577 dated Apr. 26, 2011.
Office Action for Chinese Patent Application No. 20118001186.X dated Jan. 6, 2014.
Third Office Action for Chinese Application No. 201180011860.X dated Apr. 10, 2015.
Communication dated Mar. 10, 2015, issued by the Japanese Patent Office in counterpart Application No. 2012-503175.
Communication dated Oct. 19, 2015 from the European Patent Office in counterpart application No. 11750627.9.
The Second Office Action for Chinese Patent Application No. 201180011860.X dated Sep. 26, 2014.
Office Action for Japanese Application No. 2012-503175 dated Jun. 24, 2014, with English language Excerption.
Communication dated Apr. 25, 2016 from Korean Intellectual Property Office in counterpart Application No. 10-2012-7025668.
Communication dated Oct. 13, 2016, issued by the Korean Intellectual Property Office in corresponding Korean Application No. 10-2012-7025668.
Notice of Final Rejection dated Dec. 1, 2016 issued by the Korean Patent Office in Korean Patent Application No. 10-2012-7025668.

* cited by examiner

Figure 1 Stereoscopic microscope photograph of Day 7 (chondrogenic differentiation medium) of a mosaic cell mass prepared using recombinant gelatin micro-blocks.
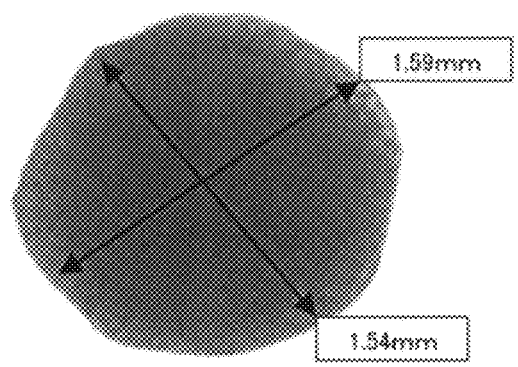
Figure 2 Stereoscopic microscope photograph of Day 7 (chondrogenic differentiation medium) of a mosaic cell mass prepared using natural gelatin micro-blocks
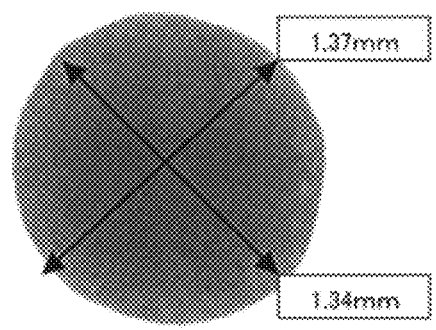

Figure 3  Photograph of a slice (HE-stained, magnification: ×5) of the mosaic cell mass containing the recombinant gelatin micro-blocks
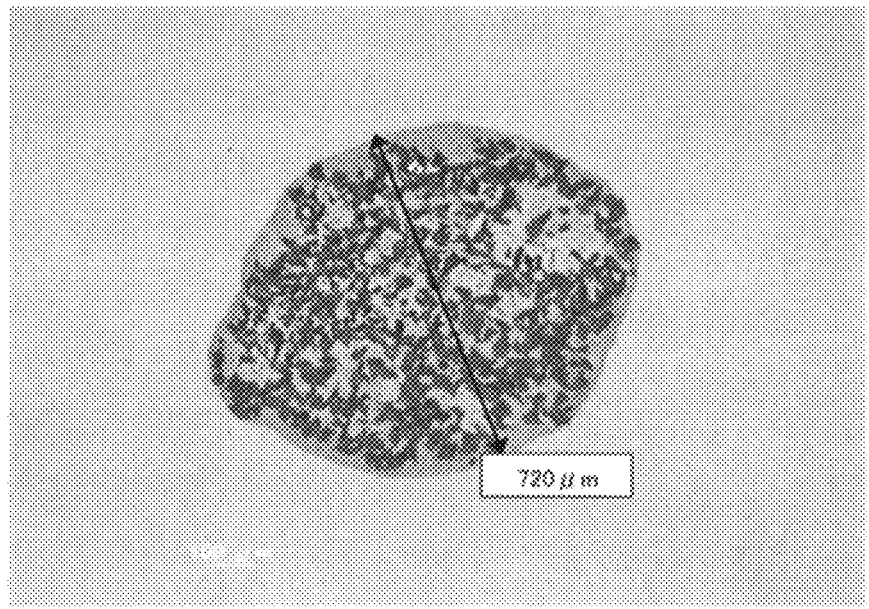
Figure 4  Photograph of a slice (HE-stained, magnification: ×10) of the mosaic cell mass containing the recombinant gelatin micro-blocks
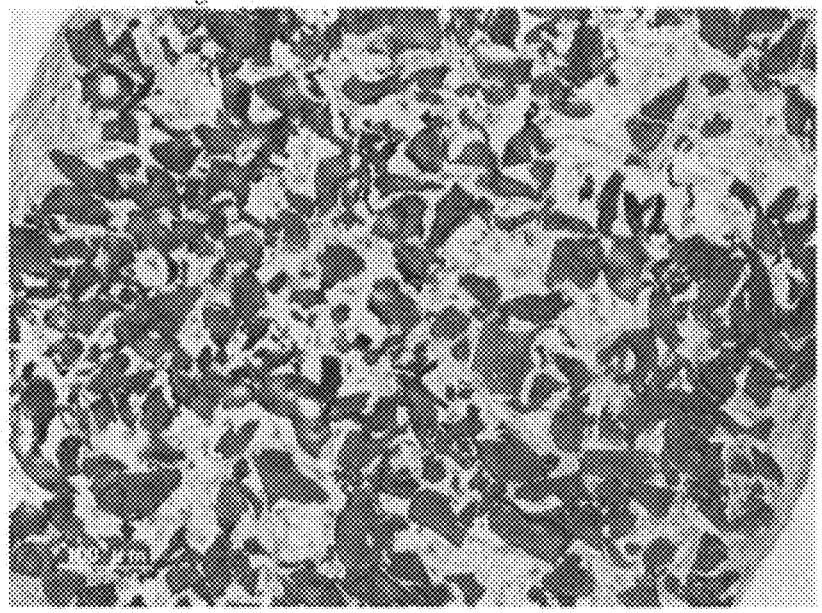

Figure 5   Photograph of a slice (HE-stained, magnification: ×40) of the mosaic cell mass containing the recombinant gelatin micro-blocks
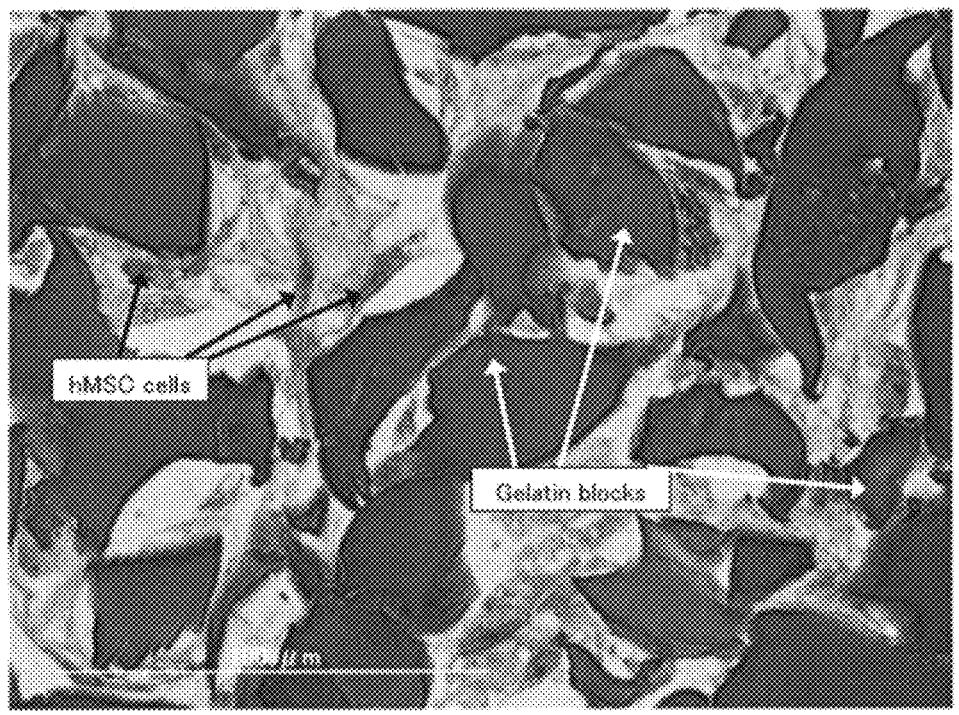

Figure 6  Fusion of the mosaic cell masses
Day 6 (first day of fusion)
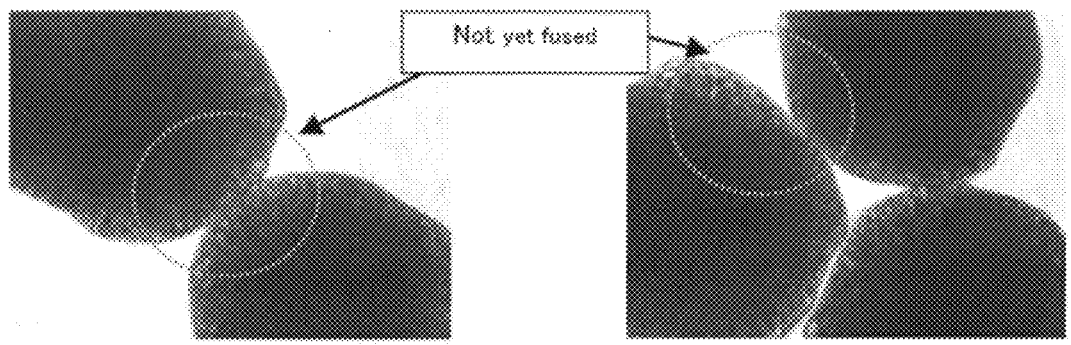
Day 11 (fifth day from the fusion)
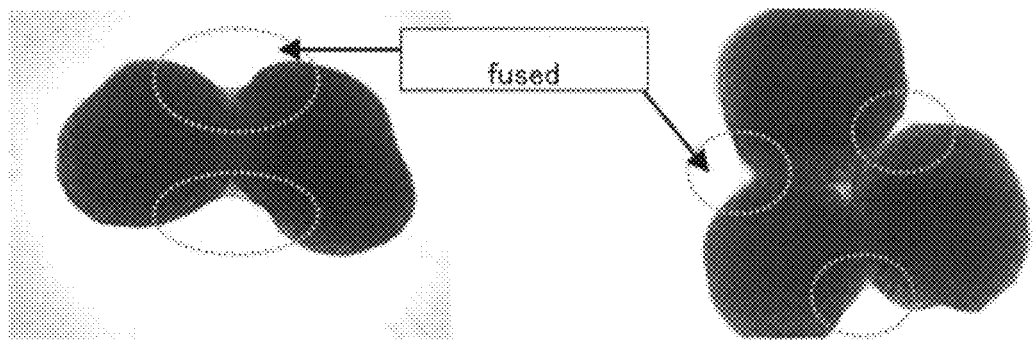
Magnified photograph at Day 11 (fifth day from the fusion)
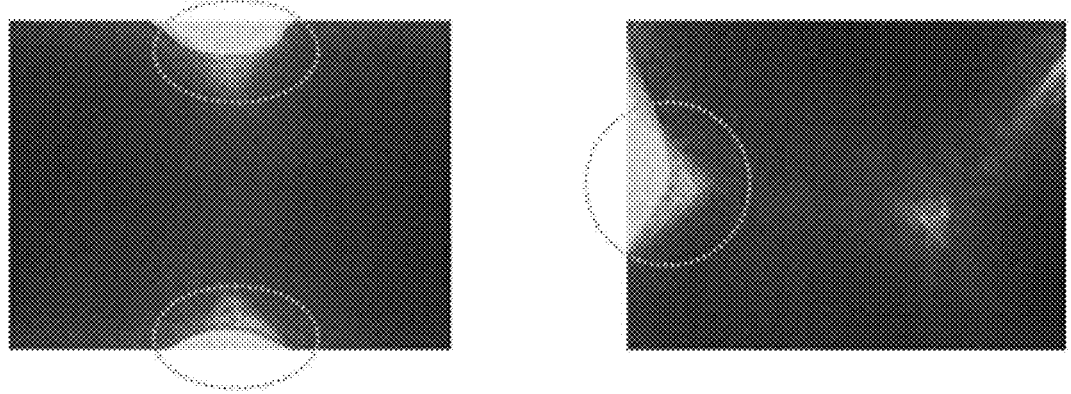

Figure 7  Photograph of a HE-stained slice (magnification: ×5) from the fusion of the mosaic cell masses (fusion of three mosaic cell masses)
Figure 8  Photograph of a HE-stained slice (magnification: ×10) from the fusion of the mosaic cell masses (fusion of three mosaic cell masses)
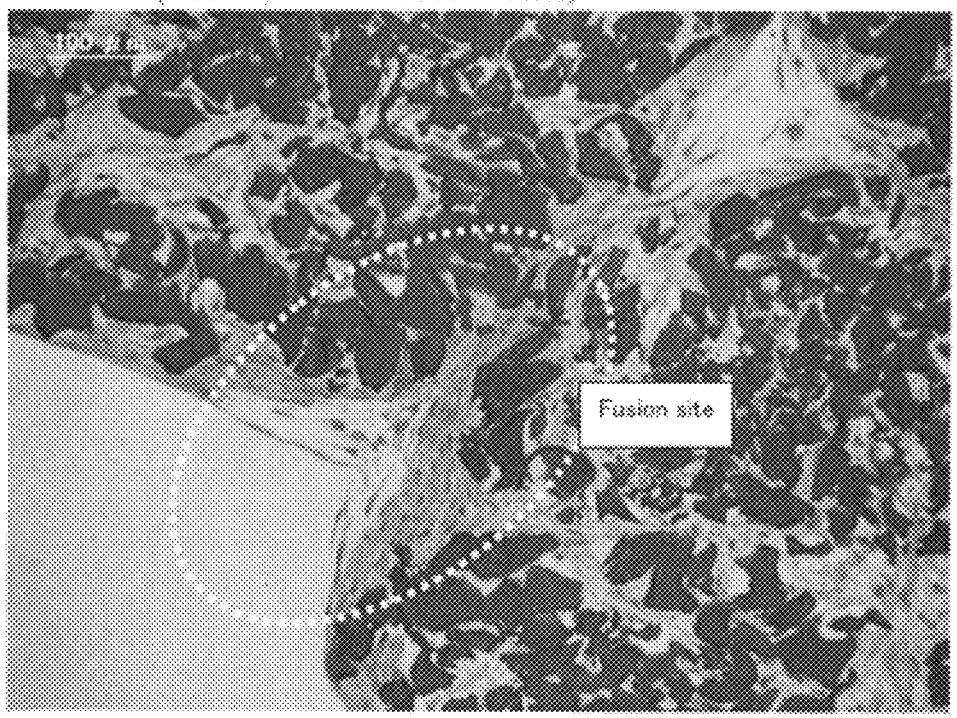

Figure 9 Photograph of a HE-stained slice (magnification: x20) from the fusion of the mosaic cell masses (fusion of three mosaic cell masses)
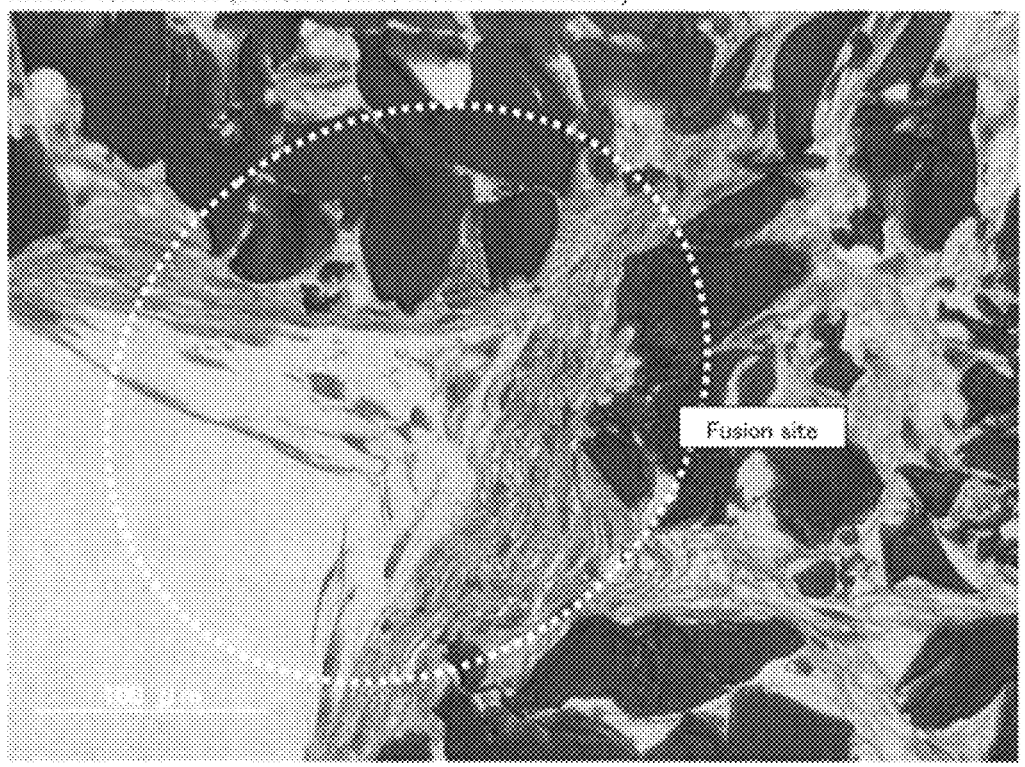

Figure 10 Photograph of a HE-stained slice (magnification: ×5) from the fusion of the mosaic cell masses (fusion of three mosaic cell masses)
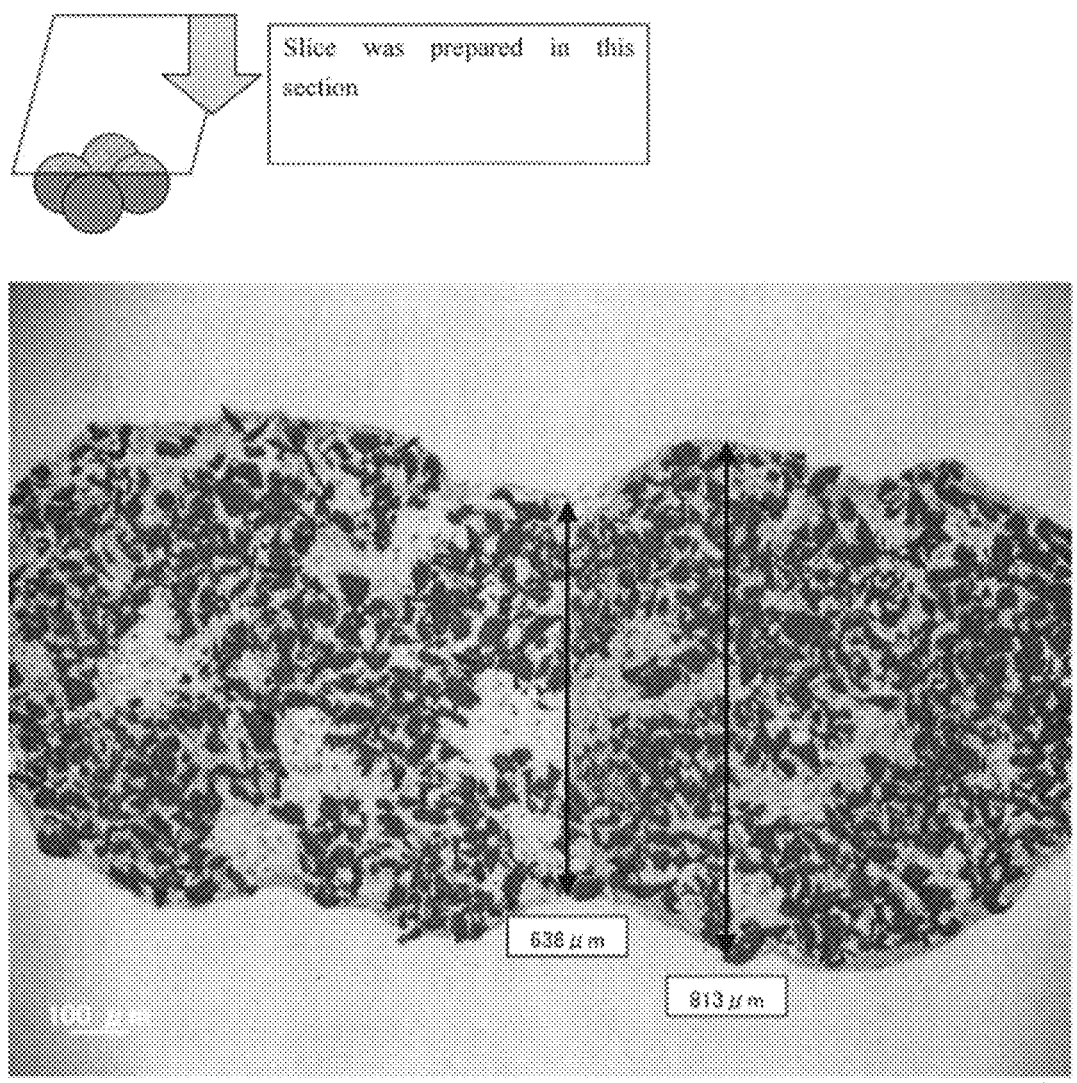

Figure 11 Photograph of a HE-stained slice (magnification: ×10) from the fusion of the mosaic cell masses (fusion of three mosaic cell masses)
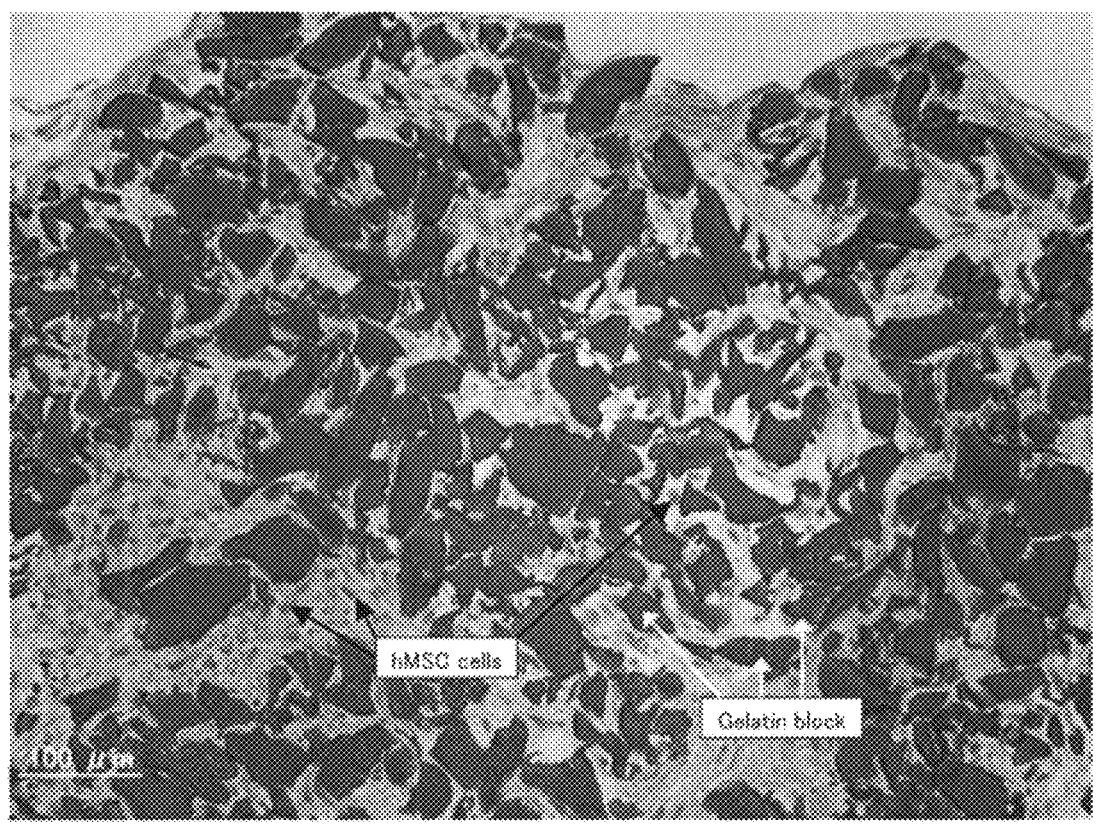

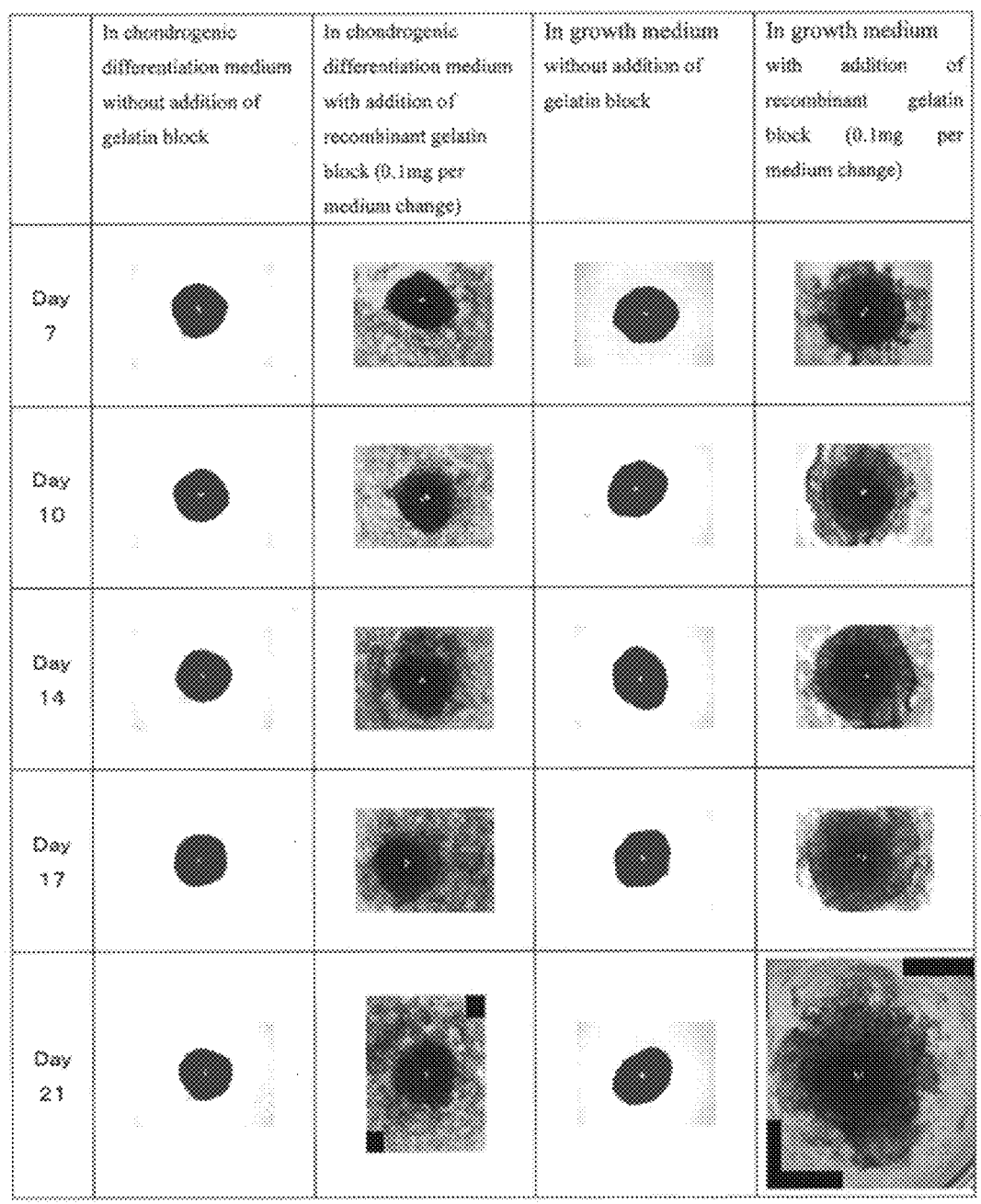
Figure 12 Stereoscopic microscope photograph (time-dependent change) of a mosaic cell mass with an increased volume.

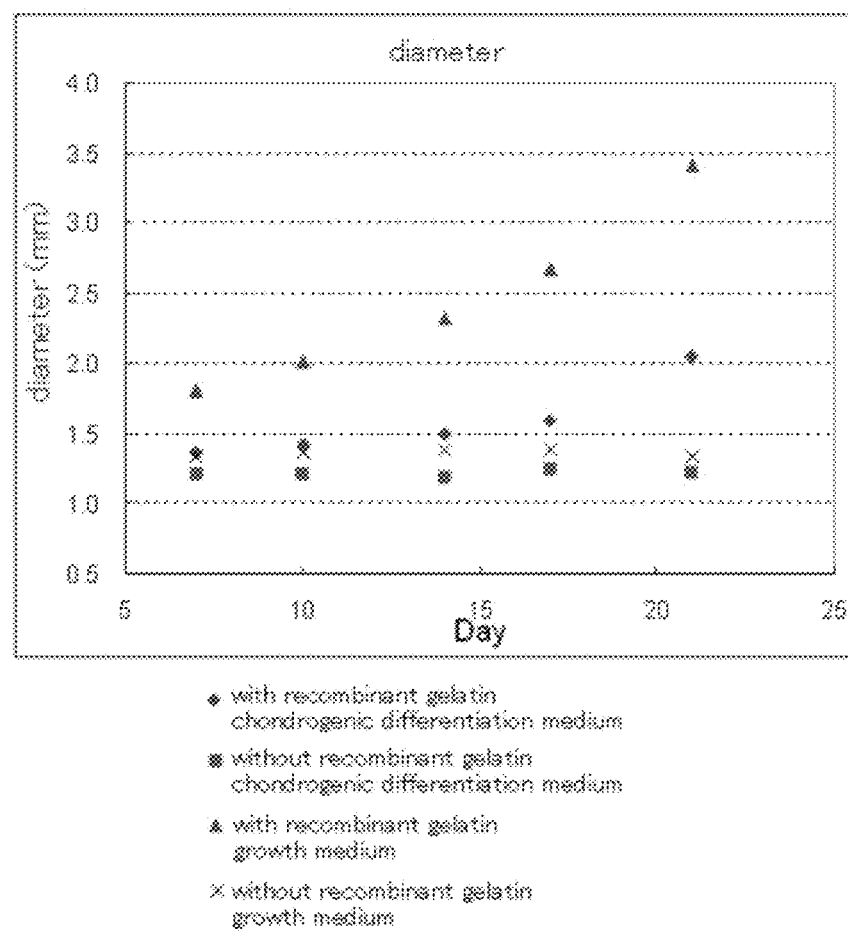
Figure 13 Time-dependent change in diameter from the stereoscopic microscope photograph of the mosaic cell mass with an increased volume

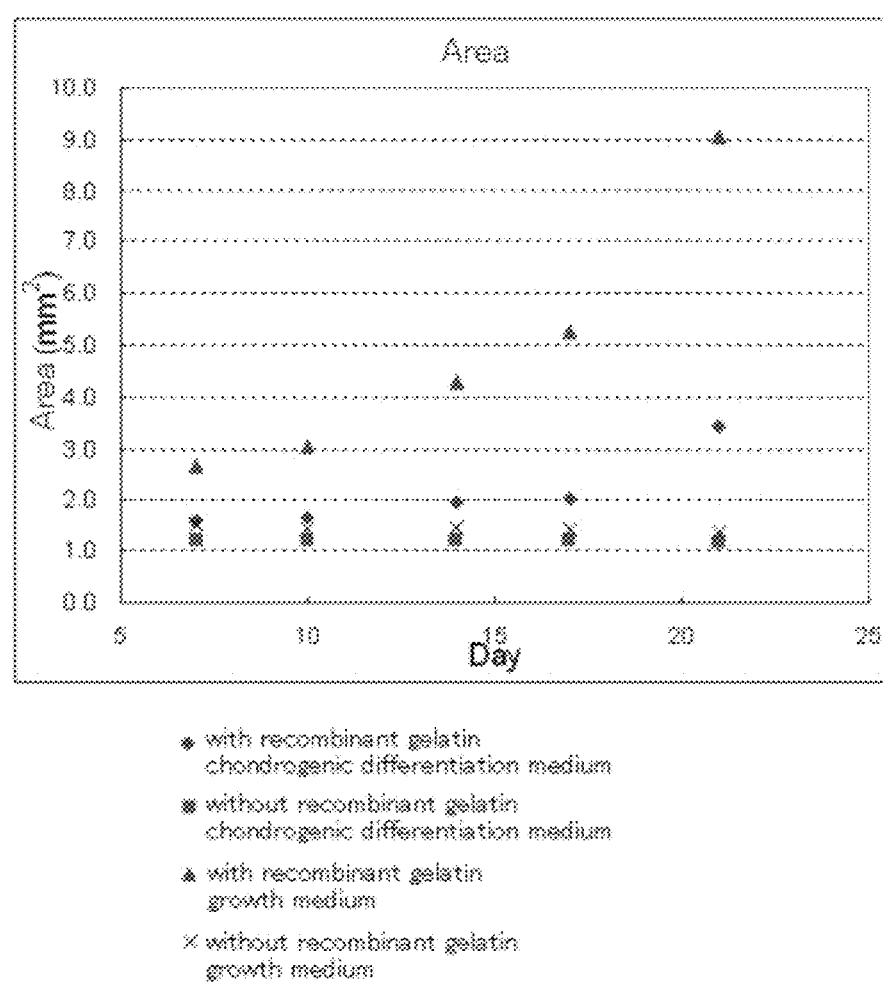
Figure 14 Time-dependent change in area from the stereoscopic microscope photograph of the mosaic cell mass with an increased volume

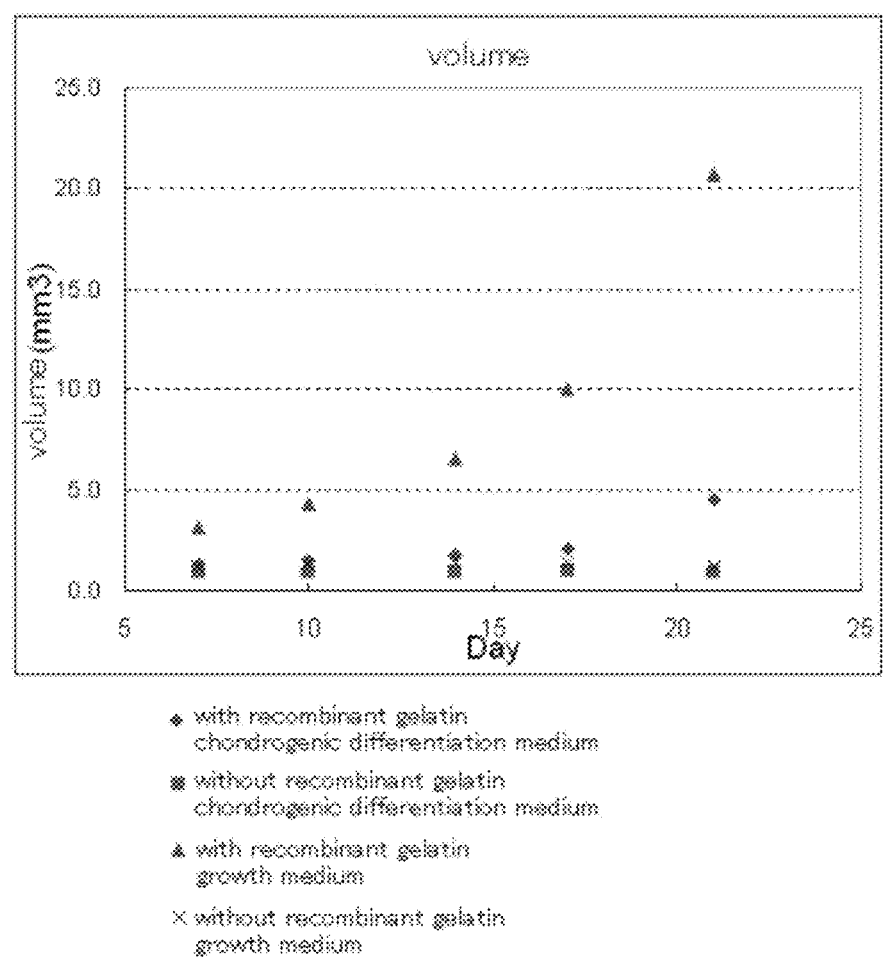
Figure 15 Time-dependent change in volume (4/3πr³) determined by calculation from the stereoscopic microscope photograph of the mosaic cell mass with an increased volume Figure 16 Slice (Day 7 (under the growth medium), magnification: ×5) of a mosaic cell mass containing the recombinant gelatin micro-blocks
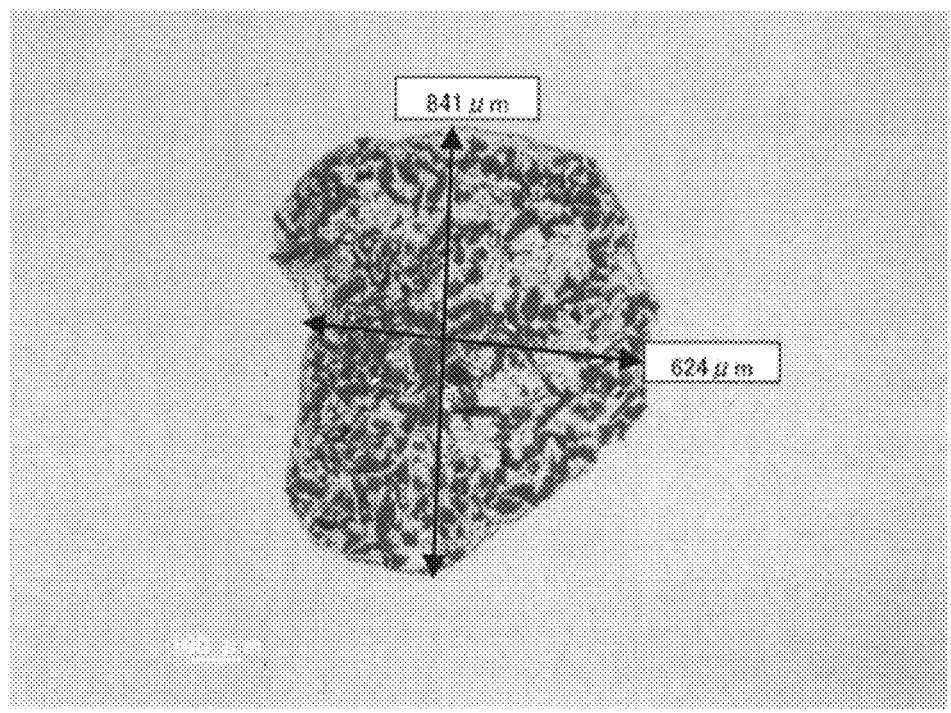

Figure 17  Slice (Day 7 (under the growth medium), magnification: ×10) of a mosaic cell mass containing the recombinant gelatin micro-blocks
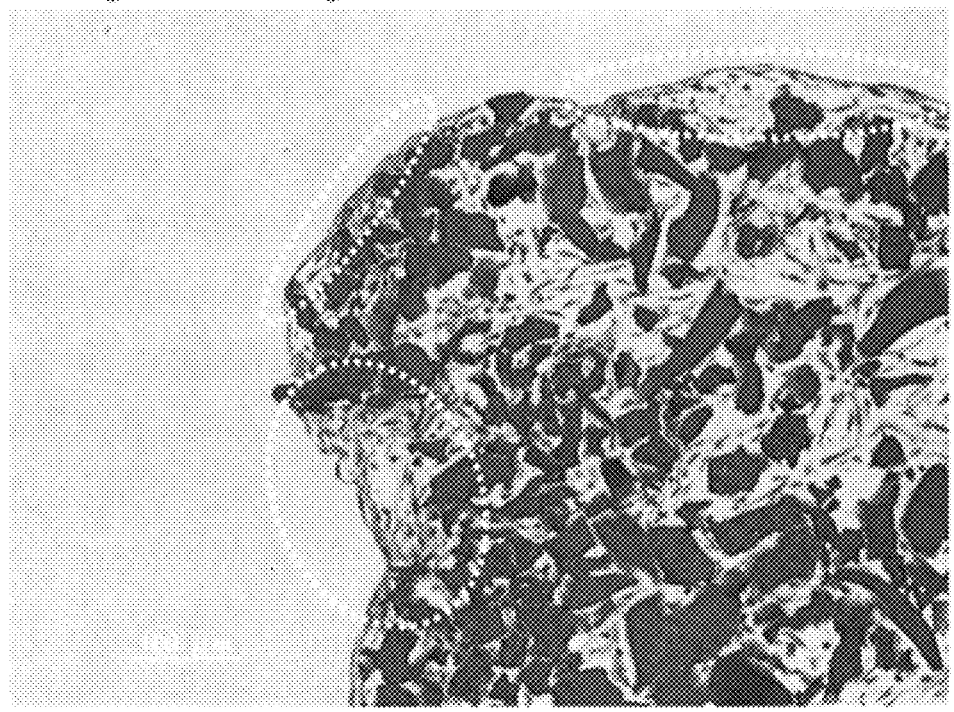
Figure 18  Photograph (magnification: ×5) of a HE slice of Day 21 with an increased volume (the recombinant gelatin blocks were added under the growth medium)
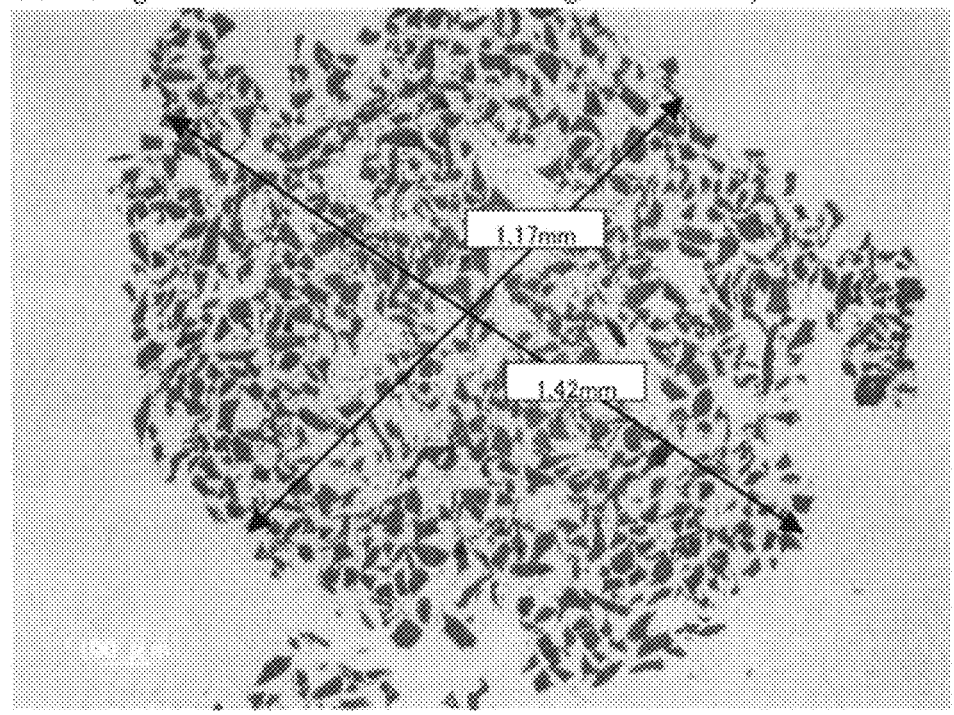

Figure 19 Photograph (magnification: ×40) of a HE slice of Day 21 with an increased volume (the recombinant gelatin blocks were added under the growth medium)
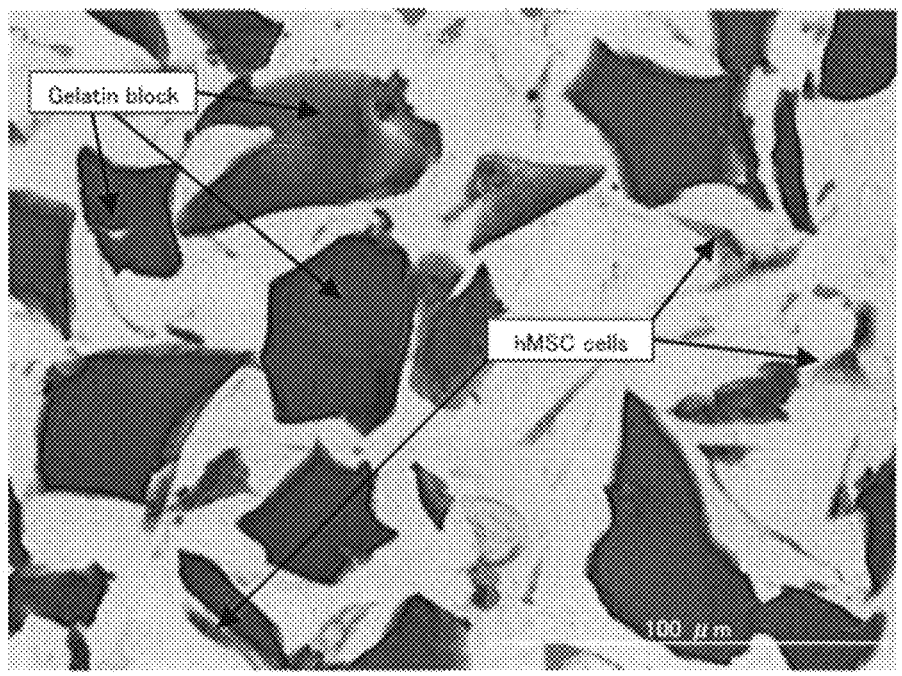

Figure 20 Photograph of a HE slice of Day 21 with an increased volume (the recombinant gelatin blocks were added under the chondrogenic differentiation medium)(magnification: ×5)
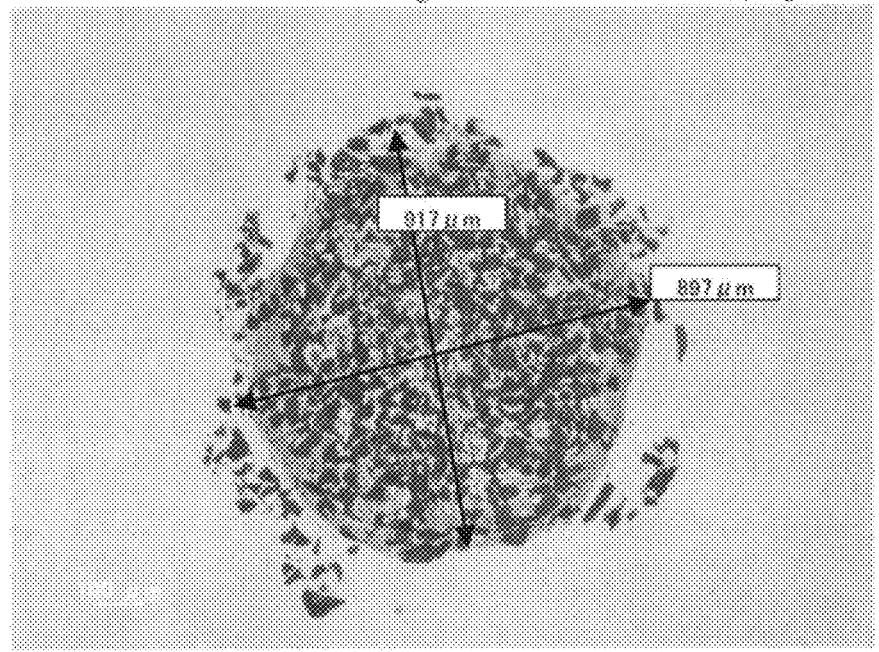
Figure 20 Photograph of a HE slice of Day 21 with an increased volume (the recombinant gelatin blocks were added under the chondrogenic differentiation medium)(magnification: ×20)
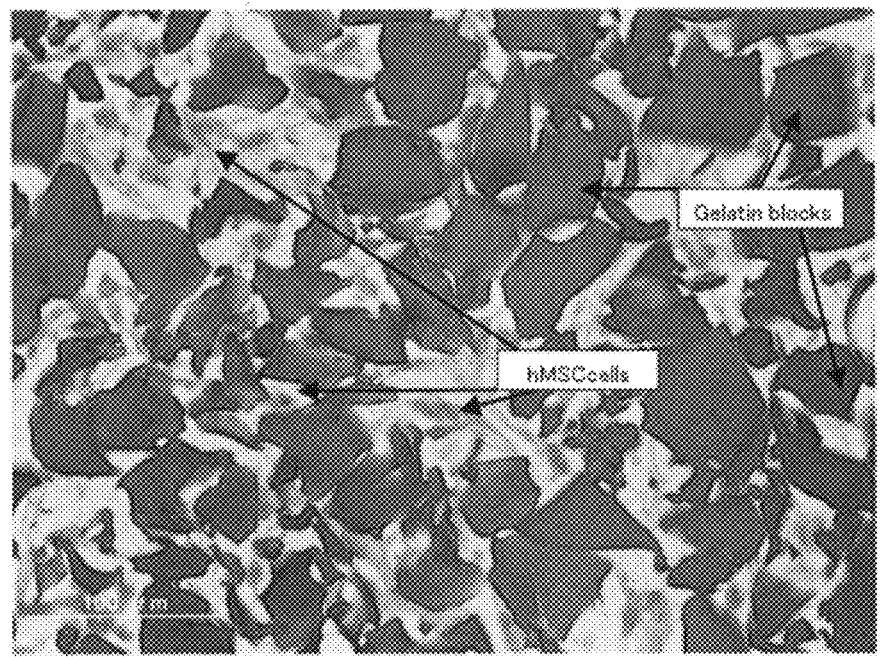

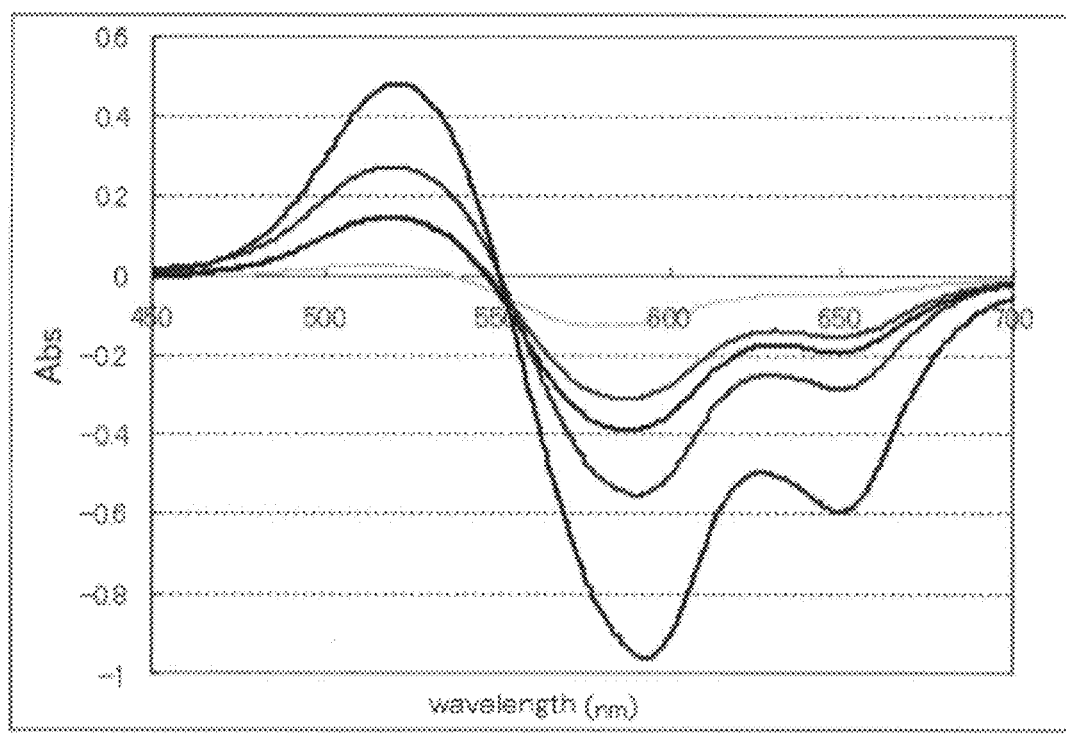
Figure 21  Spectral data of GAG

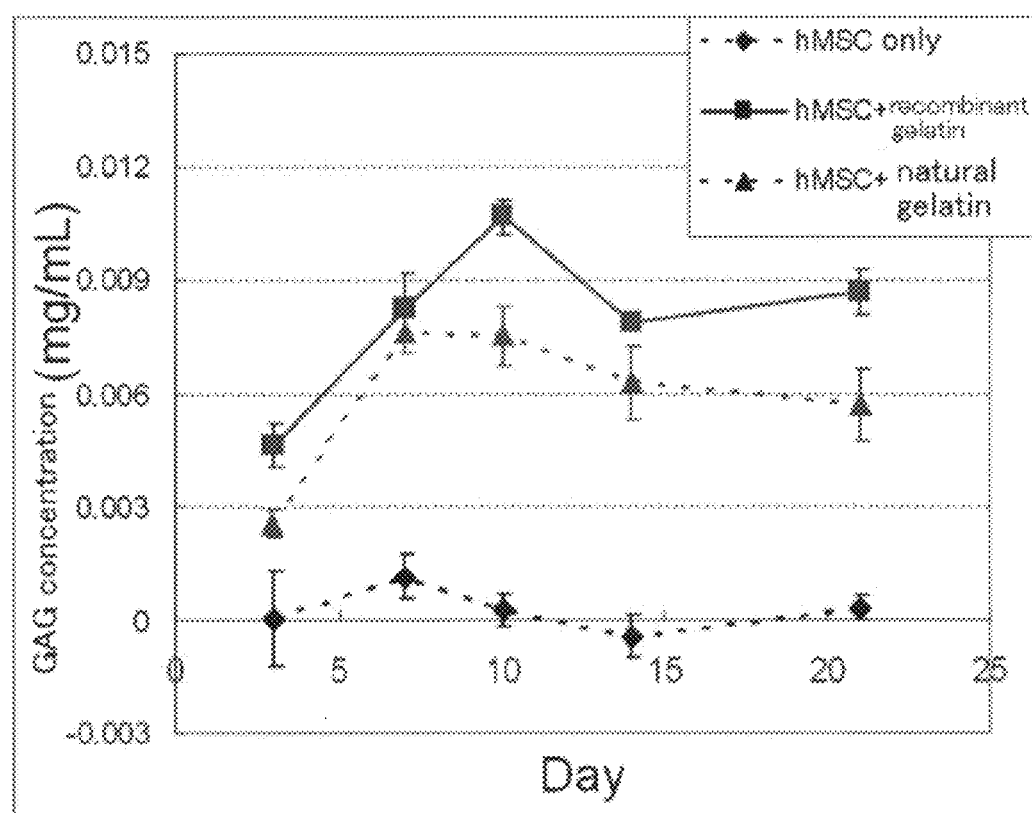
Figure 22 Time-dependent change in the amount of GAG produced in the mosaic cell mass

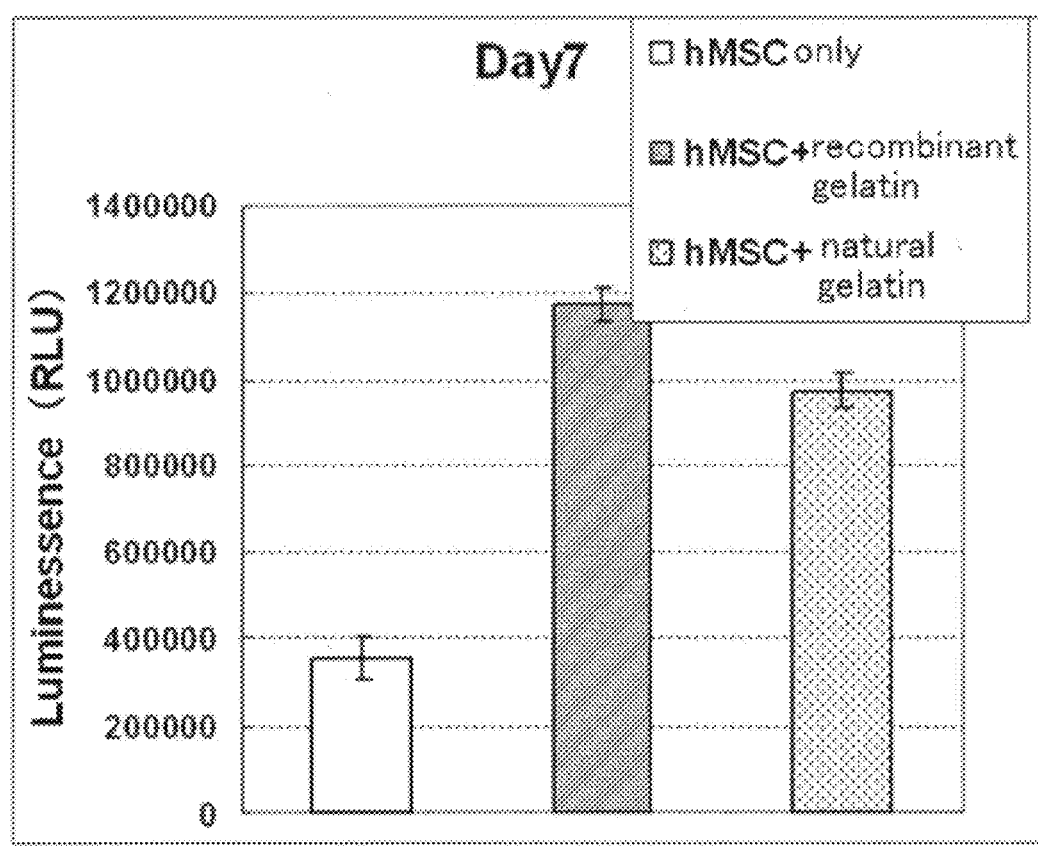
Figure 23  Amount of ATP produced/retained by the cells in the mosaic cell mass (Day 7).

Figure 24 Stereoscopic microscope photograph of Day 2 (growth medium) of a mosaic cell mass prepared using PLGA micro-blocks
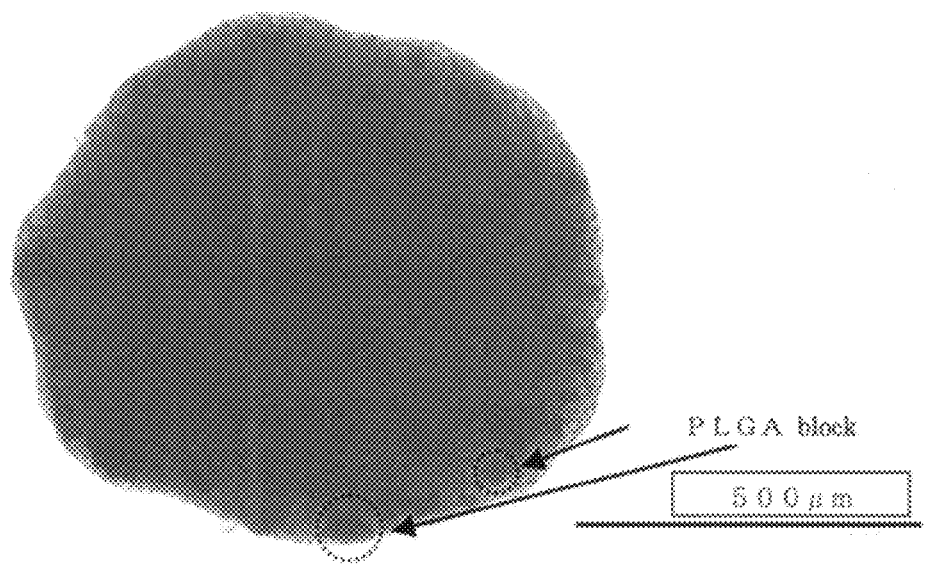

SEQUENCE LISTING

```
<160> NUMBER OF SEQ ID NOS: 1

<210> SEQ ID NO 1
<211> LENGTH: 571
<212> TYPE: PRT
<213> ORGANISM: Artificial Sequence
<220> FEATURE:
<223> OTHER INFORMATION: Synthetic peptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
```

-continued

```
            130                 135                 140
Gly Ala Pro Gly Leu Gln Gly Met Pro Gly Glu Arg Gly Ala Ala Gly
145                 150                 155                 160

Leu Pro Gly Pro Lys Gly Arg Gly Asp Ala Gly Pro Lys Gly Ala
                165                 170                 175

Asp Gly Ala Pro Gly Lys Asp Gly Val Arg Gly Leu Ala Gly Pro Pro
                180                 185                 190

Gly Ala Pro Gly Leu Gln Gly Ala Pro Gly Leu Gln Gly Met Pro Gly
            195                 200                 205

Glu Arg Gly Ala Ala Gly Leu Pro Gly Pro Lys Gly Glu Arg Gly Asp
        210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
                260                 265                 270

Asp Gly Val Arg Gly Leu Ala Gly Pro Ile Gly Pro Pro Gly Glu Arg
                275                 280                 285

Gly Ala Ala Gly Leu Pro Gly Pro Lys Gly Glu Arg Gly Asp Ala Gly
            290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
                340                 345                 350

Pro Lys Gly Glu Arg Gly Asp Ala Gly Pro Lys Gly Ala Asp Gly Ala
            355                 360                 365

Pro Gly Lys Asp Gly Val Arg Gly Leu Ala Gly Pro Pro Gly Ala Pro
            370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
                420                 425                 430

Gly Glu Arg Gly Ala Ala Gly Leu Pro Gly Pro Lys Gly Glu Arg Gly
            435                 440                 445

Asp Ala Gly Pro Lys Gly Ala Asp Gly Ala Pro Gly Lys Asp Gly Val
            450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
                500                 505                 510

Ile Gly Pro Pro Gly Pro Ala Gly Ala Pro Gly Ala Pro Gly Leu Gln
                515                 520                 525
```

-continued

```
Gly Met Pro Gly Glu Arg Gly Ala Ala Gly Leu Pro Gly Pro Lys Gly
        530                 535             540
Glu Arg Gly Asp Ala Gly Pro Lys Gly Ala Asp Gly Ala Pro Gly Lys
545             550             555             560
Asp Gly Val Arg Gly Leu Ala Gly Pro Pro Gly
            565             570
```

CELL CONSTRUCT COMPRISING POLYMER BLOCKS HAVING BIOCOMPATIBILITY AND CELLS

CROSS REFERENCE TO RELATED APPLICATIONS

This application is a National Stage of International Application No. PCT/JP2011/0574577 filed Mar. 1, 2011, claiming priority based on Japanese Patent Application Nos. 2010-044023 filed Mar. 1, 2010 and 2010-224628 filed Oct. 4, 2010, the contents of all of which are incorporated herein by reference in their entirety.

TECHNICAL FIELD

The present invention relates to a cell construct comprising polymer blocks having biocompatibility and cells in which a plurality of polymer blocks are arranged in a mosaic pattern in spaces among such plurality of cells. Also, the present invention relates to a method for producing the same.

BACKGROUND ART

The practical utilization of regenerative medicine, which helps the regeneration of living tissues/organs that have fallen into functional disorder or functional incompetence, is currently proceeding. The regenerative medicine is novel medical technology of re-creating the same or similar forms or functions as in original tissues using 3 factors, i.e., cells, scaffolds, and growth factors, for living tissues that no longer recover by only natural healing ability intrinsically possessed by organisms. In recent years, treatments using cells have been being gradually realized. Examples thereof include cultured epidermis using autologous cells, cartilage treatment using autologous cartilage cells, bone regeneration treatment using mesenchymal stem cells, cardiac muscle cell sheet treatment using myoblasts, corneal regeneration treatment using corneal epithelial sheets, and nerve regeneration treatment. These novel treatments, unlike conventional alternative medicine based on artificial materials (bone prosthetic materials or hyaluronic acid injection), help the repair or regeneration of living tissues and therefore produce high therapeutic effects. In fact, some products such as cultured epidermis or cultured cartilage using autologous cells have been launched.

However, current techniques cannot provide tissues having a sufficient thickness, because cells to be transplanted are mainly transplanted in a thin sheet form or transplanted in the state of a suspension. Living tissues are originally thick and enable muscle force to allow the heart to beat or permit smooth movement at articular cartilage because of being thick. For general tissue regeneration using cells, the inability to provide thick tissues is considered as a major problem.

For example, the regeneration of cardiac muscle using cell sheets is considered to require a multilayer construct of cell sheets for regenerating thick tissues. Okano et al. have recently developed cell sheets using a temperature-responsive culture dish. The cell sheets do not require treatment with an enzyme such as trypsin and thus retain cell-to-cell binding and adhesion proteins (Non Patent Documents 1 to 6). Such a cell sheet production technique is expected to be useful in the regeneration of cardiac muscle tissues. Since previous cell sheets cannot form vascular network, sufficiently thick tissues have been difficult to regenerate (Non Patent Documents 5 and 7). This is because nutrition supply to cells in the central portion is lost in a cell sheet which was allowed to be thick, whereby the cells are killed. Okano et al. have also thought that a thickness of 200 µm or larger is impossible to achieve, and are developing cell sheets also containing vascular endothelial cells introduced therein in order to form vascular network in the cell sheets (Non Patent Document 8). However, this cannot serve as a realistic solution due to many problems: in addition to the cells of interest, another cell source, i.e., vascular endothelial cells, must be prepared; it is difficult to uniformly induce blood vessels in the cell sheet; and even if the delivery pathway of nutrients can be provided by this means, the prepared nutrition delivery pathway must be precisely connected to an external nutrition delivery pathway in this approach.

Also for bone regeneration, bone regeneration sheets comprising cultured cells added to matrices have been developed.

A bone regeneration sheet prepared by layering a cultured cell sheet comprising mesenchymal stem cells cultured into a sheet-like shape and a biodegradable sheet comprising biodegradable substances formed into a sheet-like shape (Patent Document 1) has been proposed. Moreover, there is a sheet for induction of mesenchymal tissue regeneration in which mesenchymal tissue precursor cells differentiated from mesenchymal cells and extracellular matrices are attached onto a porous sheet (Patent Document 2). These inventions are methods involving placing a cultured osteoblast-attached sheet into the body and forming cortical bone from the osteoblast through membranous ossification in vivo. However, osteoblast-like cells cannot be cultured in a layered state, and due to this problem, sheets having an osteoblast layer have failed to provide regeneration sheets in which the thickness of a cell layer exceeds 100 µm. Then, Patent Document 3 has reported that a sheet of 200 µm or larger in thickness can be formed by the development/optimization of a culture approach, but according to this report, only the formation of approximately 210 µm cortical bone tissue layer was achieved.

As described above, it was a difficult challenge to provide cells as a thick composition for many tissue repairs. The leading cause thereof is the insufficient penetration of nutrients by only diffusion into a three-dimensional construct composed of cells. Gel-embedding culture using collagen has been devised as one means of solving this (Non Patent Document 9). However, cells embedded in a gel cannot solve this problem at its source, because the cells are moved from the central portion of the gel toward the outer region and thus, are not uniformly present in the gel so that the cell density of the central portion is reduced. Moreover, the three-dimensional cell construct prepared by gel embedding cannot be bound/fused to another three-dimensional construct and thus, cannot form a three-dimensional construct above the size prepared at the time of cell inoculation. Thus, the means of preparing small gels and then fusing the gels to each other to prepare a construct in which cells are uniformly distributed, cannot be adopted.

Moreover, Patent Document 4 states that three-dimensional culture is achieved by linking cells using inorganic ceramic beads. However, inorganic ceramics are inferior in water retention, solution exchange, diffusion of nutrition, and buffer capacity and cannot actually provide a thick cell composition. In fact, in Examples of Patent Document 4, cells were bonded to 150 to 460 µm particles, over which a thick PLLA nonwoven fabric (1 cm) was layered to merely increase an apparent thickness. The actual cell-containing layer was merely a layer of tens of µm at the thickest on the surface of the inorganic ceramic beads. Even if the 1 cm PLLA nonwoven fabric having no cell is regarded as a construct, it is merely a construct having significantly non-uniform cell distribution. Thus, only the three-dimensional cell construct having nonuniform cell distribution in the construct or the construct having a substantially thin cell layer has been provided so far.

PRIOR ART DOCUMENTS

Patent Documents

Patent Document 1: JP Patent Publication (Kokai) No. 2003-275294A (2003)
Patent Document 2: JP Patent Publication (Kokai) No. 2006-116212A (2006)
Patent Document 3: JP Patent Publication (Kokai) No. 2009-240766A (2009)
Patent Document 4: JP Patent Publication (Kokai) No. 2004-267562A (2004)

Non Patent Documents

Non Patent Document 1: Shimizu, T. et al., Circ. Res. 90, e40-48 (2002)
Non Patent Document 2: Kushida, A. et al., J. Biomed. Mater. Res. 51, 216-223 (2000)
Non Patent Document 3: Kushida, A. et al., J. Biomed. Mater. Res. 45, 355-362 (1999)
Non Patent Document 4: Shimizu, T., Yamato, M., Kikuchi, A. & Okano, T., Tissue Eng. 7, 141-151 (2001)
Non Patent Document 5: Shimizu, T et al., J. Biomed. Mater. Res. 60, 110-117 (2002)
Non Patent Document 6: Harimoto, M. et al., J. Biomed. Mater. Res. 62, 464-470 (2002)
Non Patent Document 7: Shimizu, T., Yamato, M., Kikuchi, A. & Okano, T., Biomaterials 24, 2309-2316 (2003)
Non Patent Document 8: Inflammation and Regeneration vol. 25 No. 3 2005, p. 158-159. The 26th annual meeting of the Japanese Society of Inflammation and Regeneration-Pursuing fusion between inflammation research and regenerative medicine-Mitsuo Okano
Non Patent Document 9: Sustained growth and three-dimensional organization of primary mammary tumor epithelial cells embedded in collagen gel. J Yang, J Richards, P Bowman, R Guzman, J Enami, K McCormick, S Hamamoto, D Pitelka, and S Nandi. PNAS Jul. 1, 1979 vol. 76 no. 7 3401-3405

SUMMARY OF INVENTION

Object to be Solved by the Invention

It is an object of the present invention to provide a cell construct that has a thickness sufficient for tissue regeneration and comprises cells uniformly distributed therein. It is another object of the present invention to provide a cell construct that can be produced without the use of cells other than cells of interest. It is a further object of the present invention to provide three-dimensional cell constructs that can spontaneously fuse to each other.

Means for Solving the Object

The present inventors succeeded in forming a three-dimensional cell construct that allows delivery of nutrients from the outside to the inside of the three-dimensional cell construct, has a sufficient thickness, and comprises cells uniformly distributed therein by three-dimensionally arranging bio-compatible polymer blocks (i.e., masses comprising polymeric materials having bio-compatibility) and cells in a mosaic pattern. Further, they discovered that three-dimensional cell constructs are capable of spontaneously fusing to each other through the actions of cells existing in the outer circumferences thereof. The present invention has been completed based on such findings.

The embodiments of the present invention relates to the followings.

[1] A cell construct comprising polymer blocks having biocompatibility and cells, wherein the plural polymer blocks are arranged in spaces between the plural cells.
[2] The cell construct according to [1], wherein the polymer block has a size from 1 μm to 700 μm.
[3] The cell construct according to [2], wherein the polymer block has a size from 10 μm to 300 μm.
[4] The cell construct according to any one of [1] to [3], wherein the thickness or diameter is from 400 μm to 3 cm.
[5] The cell construct according to [4], wherein the thickness or diameter is from 720 μm to 1 cm.
[6] The cell construct according to any one of [1] to [5], wherein the ratio between the polymer blocks and the cells is from 0.0000001 μg to 1 μg of the polymer blocks per cell.
[7] The cell construct according to any one of [1] to [6], which is produced by incubating a mixture of the polymer blocks having biocompatibility and a culture solution comprising the cells.
[8] The cell construct according to any one of [1] to [7], wherein the polymer having biocompatibility is a biodegradable material.
[9] The cell construct according to any one of [1] to [8], wherein the polymer having biocompatibility is polypeptide, polylactic acid, polyglycolic acid, PLGA, hyaluronic acid, glycosaminoglycan, proteoglycan, chondroitin, cellulose, agarose, carboxymethylcellulose, chitin, or chitosan.
[10] The cell construct according to any one of [1] to [9], wherein the polymer having biocompatibility is gelatin, collagen, elastin, fibronectin, ProNectin, laminin, tenascin, fibrin, fibroin, entactin, thrombospondin, or RetroNectin.
[11] The cell construct according to any one of [1] to [10], wherein the polymer having biocompatibility is cross-linked.
[12] The cell construct according to [11], wherein the cross-linking is performed with an aldehyde, a condensing agent, or an enzyme.
[13] The cell construct according to any one of [1] to [12], wherein the polymer having biocompatibility is a recombinant gelatin.
[14] The cell construct according to [13], wherein the polymer having biocompatibility has two or more cell adhesion signals in a molecule.
[15] The cell construct according to [13], wherein the recombinant gelatin is represented by the formula:

A-[(Gly-X-Y)$_n$]$_m$-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X-Y of total n may be the same as or different from each other.
[16] The cell construct according to [13] or [15], wherein the recombinant gelatin is represented by the formula:

Gly-Ala-Pro-[(Gly-X-Y)$_{63}$]$_3$-Gly wherein each X of total 63 independently represents any amino acid; each Y of total 63 independently represents any amino acid; and each Gly-X-Y of total 63 may be the same as or different from each other.

[17] The cell construct according to any one of [13] to [16], wherein the recombinant gelatin has any of the followings: (1) the amino acid sequence represented by SEQ ID NO: 1, or (2) an amino acid sequence having 80% or higher homology to the amino acid sequence represented by SEQ ID NO: 1 and having biocompatibility.

[18] The method for producing a cell construct according to any of [1] to [17], which comprises a step of incubating a mixture of polymer blocks having biocompatibility and a cell-containing culture solution.

[19] The method according to [18], wherein the step of incubating a mixture of polymer blocks having biocompatibility and a cell-containing culture solution comprises exchanging a medium with a fresh medium.

[20] The method according to [19], wherein the step of incubating a mixture of polymer blocks having biocompatibility and a cell-containing culture solution comprises exchanging a medium with a differentiation or growth medium.

[21] The method according to any one of [18] to [20], wherein the step of incubating a mixture of polymer blocks having biocompatibility and a cell-containing culture solution further comprises further adding polymer blocks having biocompatibility.

[22] A cell construct which is produced by the method according to any one of [18] to [21].

[23] A cell construct which is obtained by fusion of a plurality of the cell constructs according to any of [1] to [17].

[24] A method for producing the cell construct according to [23], which comprises a step of subjecting a plurality of the cell constructs according to any of [1] to [17] to fusion.

[25] A method for producing a cell construct which comprises a step of fusion of a plurality of cell constructs that comprise a plurality of polymer blocks having biocompatibility and a plurality of cells wherein 1 or a plurality of polymer blocks are arranged in some or all of a plurality of spaces formed by the plurality of cells.

[26] The method for producing a cell construct according to [25], wherein the size of the polymer block is between 1 μm and 700 μm.

[27] The method for producing a cell construct according to [25] or [26], wherein the thickness or diameter of a cell construct is between 10 μm and 1 cm before fusion, and the thickness or diameter of a cell construct is between 400 μm and 3 cm after fusion.

[28] A method for producing a cell construct which comprises a step of further adding a second polymer block to a cell construct that comprises a plurality of first polymer blocks having biocompatibility and a plurality of cells wherein 1 or a plurality of polymer blocks are arranged in some or all of a plurality of spaces formed by the plurality of cells, and incubating the same.

[29] The method for producing a cell construct according to [28], wherein the size of the first polymer block is between 1 μm and 700 μm.

[30] The method for producing a cell construct according to [28] or [29], wherein the size of the second polymer block is between 1 μm and 700 μm.

[31] The method for producing a cell construct according to any one of [28] to [30], wherein the thickness or diameter is between 400 μm and 3 cm after the addition of the second polymer block and incubation.

[32] A cell construct which is produced by the method for producing a cell construct according to any one of [25] to [31].

[33] The cell construct according to [32], which is used for cell transplantation, cell culture, or virulence evaluation.

Effect of the Invention

The cell construct of the present invention has a thickness sufficient for tissue regeneration and comprises cells uniformly distributed therein. The cell construct of the present invention can be produced without the use of cells other than cells of interest. Further, the cell constructs of the present invention are capable of spontaneously fusing to each other. The cell construct of the present invention is useful for regenerative medicine aimed at regeneration of biological tissue or organs suffering from impairment or dysfunction.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows a stereoscopic microscope photograph of Day 7 (chondrogenic differentiation medium) of a mosaic cell mass prepared using recombinant gelatin micro-blocks.

FIG. 2 shows a stereoscopic microscope photograph of Day 7 (chondrogenic differentiation medium) of a mosaic cell mass prepared using natural gelatin micro-blocks.

FIG. 3 shows a photograph of a slice (HE-stained, magnification: ×5) of the mosaic cell mass containing the recombinant gelatin micro-blocks.

FIG. 4 shows a photograph of a slice (HE-stained, magnification: ×10) of the mosaic cell mass containing the recombinant gelatin micro-blocks.

FIG. 5 shows a photograph of a slice (HE-stained, magnification: ×40) of the mosaic cell mass containing the recombinant gelatin micro-blocks.

FIG. 6 shows the fusion of the mosaic cell masses.

FIG. 7 shows a photograph of a HE-stained slice (magnification: ×5) from the fusion of the mosaic cell masses (fusion of three mosaic cell masses).

FIG. 8 shows a photograph of a HE-stained slice (magnification: ×10) from the fusion of the mosaic cell masses (fusion of three mosaic cell masses).

FIG. 9 shows a photograph of a HE-stained slice (magnification: ×20) from the fusion of the mosaic cell masses (fusion of three mosaic cell masses).

FIG. 10 shows a photograph of a HE-stained slice (magnification: ×5) from the fusion of the mosaic cell masses (fusion of three mosaic cell masses).

FIG. 11 shows a photograph of a HE-stained slice (magnification: ×10) from the fusion of the mosaic cell masses (fusion of three mosaic cell masses).

FIG. 12 shows a stereoscopic microscope photograph (time-dependent change) of a mosaic cell mass with an increased volume.

FIG. 13 shows time-dependent change in diameter from the stereoscopic microscope photograph of the mosaic cell mass with an increased volume.

FIG. 14 shows time-dependent change in area from the stereoscopic microscope photograph of the mosaic cell mass with an increased volume.

FIG. 15 shows time-dependent change in volume ($4/3\pi r^3$) determined by calculation from the stereoscopic microscope photograph of the mosaic cell mass with an increased volume.

FIG. 16 shows a slice (Day 7 (under the growth medium), magnification: ×5) of a mosaic cell mass containing the recombinant gelatin micro-blocks.

FIG. 17 shows a slice (Day 7 (under the growth medium), magnification: ×10) of a mosaic cell mass containing the recombinant gelatin micro-blocks.

FIG. 18 shows a photograph (magnification: ×5) of a HE slice of Day 21 with an increased volume (the recombinant gelatin blocks were added under the growth medium).

FIG. 19 shows a photograph (magnification: ×40) of a HE slice of Day 21 with an increased volume (the recombinant gelatin blocks were added under the growth medium).

FIG. 20 shows a photograph (magnification: ×5 and ×20) of a HE slice of Day 21 with an increased volume (the recombinant gelatin blocks were added under the chondrogenic differentiation medium).

FIG. 21 shows spectral data of GAG

FIG. 22 shows time-dependent change in the amount of GAG produced in the mosaic cell mass.

FIG. 23 shows the amount of ATP produced/retained by the cells in the mosaic cell mass (Day 7).

FIG. 24 shows a stereoscopic microscope photograph of Day 2 (growth medium) of a mosaic cell mass prepared using PLGA micro-blocks.

EMBODIMENTS FOR CARRYING OUT THE INVENTION

Figure 25:
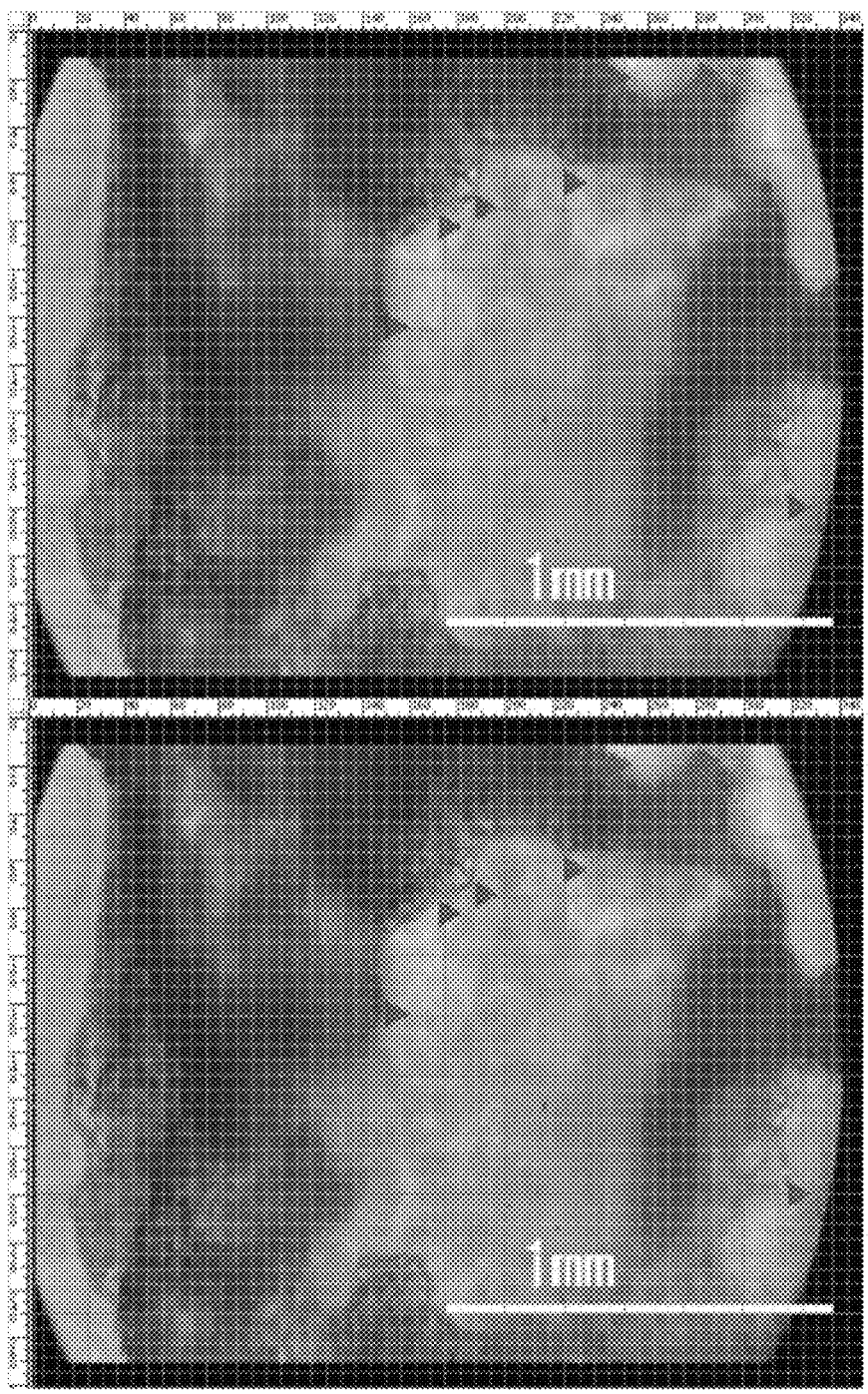
FIG. 25 shows the manner in which a mosaic cell mass consisting of cardiac muscle cells and the recombinant gelatin micro-blocks beats in synchronization as a whole.

Hereinafter, the embodiments of the present invention will be described in detail.

The cell construct of the present invention comprises polymer blocks having biocompatibility and cells, wherein the plural polymer blocks are arranged in spaces between the plural cells. Examples of an aspect thereof include a cell construct comprising plural polymer blocks having biocompatibility and plural cells, wherein one or plural polymer blocks are arranged in some or all of plural spaces formed by the plural cells.

The shape of the polymer blocks according to the present invention is not particularly limited and is, for example, amorphous, spherical, particulate, powdery, porous, fibrous, spindle-like, flat, and sheet-like shapes, preferably amorphous, spherical, particulate, powdery, and porous shapes, more preferably an amorphous shape. The term "amorphous" represents a nonuniform surface shape, for example, matter having surface irregularities, such as rocks.

In the cell construct of the present invention, the plural polymer blocks are arranged in spaces between the plural cells. In this context, the "spaces between the cells" do not have to be closed spaces created by the constituent cells and need only to be flanked by the cells. It is not required that all the cells should create such spaces therebetween. There may be a region in which the cells are in contact with each other. The distance of each space between the cells via the polymer block(s), i.e., the distance of the space from a certain cell to a selected cell located nearest from the certain cell, is not particularly limited and is preferably, the size of one cell used or a cell mass containing a cell population, for example, from 10 µm to 1000 µm, preferably from 10 µm to 100 µm, more preferably from 10 µm to 50 µm.

polymer block(s). The preferable distance is also in the range of preferable sizes of the polymer block(s).

Moreover, the polymer blocks according to the present invention are flanked by the cells in the constitution. It is not required that cells are present between all the polymer blocks. There may be a region in which the polymer blocks are in contact with each other. The distance between the polymer blocks via the cell(s), i.e., the distance from a certain polymer block to a selected polymer block located nearest from the certain polymer block, is not particularly limited and is preferably the size of one cell used or a cell mass containing a cell population, for example, from 10 µm to 1000 µm, preferably from 10 µm to 100 µm, more preferably from 10 µm to 50 µm.

(1) Polymer Material Having Biocompatibility (1-1) Polymer Material

The polymer having biocompatibility used in the present invention is not particularly limited by whether or not the polymer is degraded in vivo as long as it has affinity for organisms. It is preferred to be composed of a biodegradable material. A non-biodegradable material is specifically at least one material selected from the group consisting of PTFE, polyurethane, polypropylene, polyester, vinyl chloride, polycarbonate, acryl, stainless, titanium, silicone, and MPC. A biodegradable material is specifically at least one material selected from the group consisting of polypeptide, polylactic acid, polyglycolic acid, PLGA, hyaluronic acid, glycosaminoglycan, proteoglycan, chondroitin, cellulose, agarose, carboxymethylcellulose, chitin, and chitosan. Among them, polypeptide is particularly preferable. In this context, these polymer materials may be given a contrivance to enhance cell adhesiveness. Methods such as [1] "coating of matrix surface with a cell-adhesive substrate (fibronectin, vitronectin, and laminin) or a cell adhesion sequence (RGD sequence, LDV sequence, REDV sequence, YIGSR sequence, PDSGR sequence, RYVVLPR sequence, LGTIPG sequence, RNIAEIIKDI sequence, IKVAV sequence, LRE sequence, DGEA sequence, and HAV sequence, indicated by single letter codes for amino acids) peptide", [2] "amination or cationization of matrix surface", and [3] "plasma treatment or corona discharge-based hydrophilic treatment of matrix surface" may be used as specific methods.

The type of the polypeptide is not particularly limited as long as it has biocompatibility. The polypeptide is preferably, for example, gelatin, collagen, elastin, fibronectin, ProNectin, laminin, tenascin, fibrin, fibroin, entactin, thrombospondin, or RetroNectin, most preferably gelatin, collagen, or atelocollagen. Natural gelatin or a recombinant gelatin is preferable as gelatin for use in the present invention. A recombinant gelatin is more preferable. In this context, the natural gelatin means gelatin formed from naturally derived collagen. The recombinant gelatin will be described later in the present specification.

The hydrophilicity value "1/IOB" value of the polymer having biocompatibility used in the present invention is preferably 0 to 1.0, more preferably 0 to 0.6, further preferably 0 to 0.4. IOB is an index for hydrophilicity and hydrophobicity based on the organic conception diagram representing the polarity/non-polarity of organic compounds proposed by Atsushi Fujita. The details thereof are described in, for example, "Pharmaceutical Bulletin", vol. 2, 2, pp. 163-173 (1954), "Journal of Japanese Chemistry" vol. 11, 10, pp. 719-725 (1957), and "Fragrance Journal", vol. 50, pp. 79-82 (1981). In short, this process involves assuming that methane ($CH_4$) is the source of all organic compounds and all of the other compounds are methane derivatives, selecting a certain numerical value for each of the number of carbon atoms, substituents, modified moieties, rings and the like thereof, adding the scores to determine an organic value (OV) and an inorganic value (IV), and plotting this value on a diagram with the organic value on the X axis and the inorganic value on the Y axis. IOB on the organic conception diagram refers to the ratio of the inorganic value (IV) to the organic value (OV), i.e., "inorganic value (IV)/organic value (OV)", on the organic conception diagram. For the details of the organic conception diagram, see "Shinban Yuuki Gainenzu—Kiso to Ouyou—(New Edition, The Organic Conceptual Diagram, its Fundamentals and Applications in English)", (Yoshio Koda et al., Sankyo Publishing Co., Ltd., 2008)". In the present specification, hydrophilicity and hydrophobicity are indicated by "1/IOB" values, reciprocals of JOB. This notation represents that the smaller the "1/IOB" value becomes (the more the "1/IOB" value approaches 0), the more hydrophilic it is.

The "1/IOB" value of the polymer used in the present invention is set to within the range described above, whereby hydrophilicity is enhanced and water absorbability is enhanced. The resulting polymer is presumed to effectively act on retention of nutrients and, as a result, contribute to cell stabilization and viability in the three-dimensional cell construct (mosaic cell mass) of the present invention.

In the case where the polymer having biocompatibility used in the present invention is polypeptide, its index for hydrophilicity and hydrophobicity indicated by Grand average of hydropathicity (GRAVY) values is preferably from −9.0 to 0.3, more preferably from −7.0 to 0.0. The Grand average of hydropathicity (GRAVY) value can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

The GRAVY value of the polymer used in the present invention is set to within the range described above, whereby hydrophilicity is enhanced and water absorbability is enhanced. The resulting polymer is presumed to effectively act on retention of nutrients and, as a result, contribute to cell stabilization and viability in the three-dimensional cell construct (mosaic cell mass) of the present invention.

(1-2) Cross-Linking

The polymer material having biocompatibility used in the present invention may be cross-linked or may not be cross-linked. Those cross-linked are preferable. Any method known in the art, such as thermal cross-linking, chemical cross-linking, cross-linking using an aldehyde (e.g., formaldehyde and glutaraldehyde), cross-linking using a condensing agent (carbodiimide, cyanamide, etc.), enzymatic cross-linking, photocrosslinking, UV cross-linking, hydrophobic interaction, hydrogen bond, or ionic interaction can be used as a cross-linking method. A cross-linking method using glutaraldehyde or a thermal cross-linking method is preferable.

Examples of the photocrosslinking include those based on light irradiation of a polymer containing a photoreactive group introduced therein, or light irradiation in the presence of a photosensitizer. Examples of the photoreactive group include a cinnamyl group, a coumarin group, a dithiocarbamyl group, a xanthene dye, and camphorquinone.

In the case of performing cross-linking using an enzyme, the enzyme is not particularly limited as long as it has the effect of cross-linking between polymer materials. The cross-linking can be performed using preferably transglutaminase and laccase, most preferably transglutaminase. Specific examples of proteins that may be subjected to enzymatic cross-linking with transglutaminase are not particularly limited as long as they are proteins having a lysine residue and a glutamine residue. The transglutaminase may be derived from a mammal or may be derived from a microbe. Specific examples thereof include ACTIVA series manufactured by Ajinomoto Co., Inc., mammal-derived transglutaminase sold as reagents, for example, guinea pig liver-derived transglutaminase, goat-derived transglutaminase, and rabbit-derived transglutaminase manufactured by Oriental Yeast Co., ltd., Upstate USA Inc., or Biodesign International, and human-derived blood coagulation factor (Factor XIIIa, Haematologic Technologies, Inc.).

The cross-linking of the polymer material involves two steps: a step of mixing a polymer material solution with a cross-linking agent and a step of reacting the resulting solution.

In the present invention, the mixing temperature for the treatment of polymer materials with a cross-linking agent is not particularly limited as long as the solution can be mixed. The temperature is preferably 0° C. to 100° C., more preferably 0° C. to 40° C., further preferably 0° C. to 30° C., further preferably 3° C. to 25° C., further preferably 3° C. to 15° C., further preferably 3° C. to 10° C., particularly preferably 3° C. to 7° C.

The temperature can be raised for the step of reacting the polymer materials with the cross-linking agent. The reaction temperature is not particularly limited as long as the cross-linking proceeds. In consideration of the denaturation or degradation of the polymer materials, the temperature is substantially −100° C. to 200° C., more preferably 0° C. to 60° C., more preferably 0° C. to 40° C., further preferably 3° C. to 25° C., further preferably 3° C. to 15° C., further preferably 3° C. to 10° C., particularly preferably 3° C. to 7° C.

Even if the cross-linking agent is not used, the cross-linking of the polymer material can also be performed. Specific examples of the cross-linking method include, but not particularly limited to, a thermal cross-linking method.

The reaction temperature for the cross-linking method without using the cross-linking agent is not particularly limited as long as the cross-linking can be performed. The temperature is preferably −100° C. to 500° C., more preferably 0° C. to 300° C., further preferably 50° C. to 300° C., further preferably 100° C. to 250° C., further preferably 120° C. to 200° C.

(1-3) Recombinant Gelatin

The recombinant gelatin in the present invention means a polypeptide or a protein-like substance that is prepared by a gene recombination technique and has an amino acid sequence similar to gelatin. For the recombinant gelatin that can be used in the present invention, it is preferred to have repeats of the sequence represented by Gly-X-Y (X and Y each independently represent any amino acid) characteristic of collagen (a plurality of Gly-X-Y sequences may be the same as or different from each other). Preferably, two or more sequences of cell adhesion signals are contained in a molecule. A recombinant gelatin having an amino acid sequence derived from a partial amino acid sequence of collagen can be used as the recombinant gelatin used in the present invention. For example, those described in EP1014176, U.S. Pat. No. 6,992,172, WO2004/85473, and WO2008/103041 can be used, though the recombinant gelatin is not limited to them. A preferable recombinant gelatin used in the present invention is a recombinant gelatin having the following aspect:

The recombinant gelatin used in the present invention is excellent in biocompatibility based on the original performance of natural gelatin, is free from concerns about BSE or the like because of being not naturally derived, and is also excellent in non-infectious properties. Moreover, since the recombinant gelatin used in the present invention is homogeneous compared with natural one and its sequence is determined, it can be designed precisely with a little variation in strength or degradability depending on cross-linking or the like described later.

The molecular weight of the recombinant gelatin is preferably from 2 KDa to 100 KDa, more preferably from 2.5 KDa to 95 KDa, further preferably from 5 KDa to 90 KDa, most preferably from 10 KDa to 90 KDa.

The recombinant gelatin has repeats of the sequence represented by Gly-X-Y characteristic of collagen. In this context, a plurality of Gly-X-Y sequences may be the same as or different from each other. In Gly-X-Y, Gly represents glycine, and X and Y each represent any amino acid (preferably, any amino acid other than glycine). The GXY sequence characteristic of collagen is a very specific partial structure in the amino acid composition and sequence of gelatin/collagen, compared with other proteins. In this moiety, glycine accounts for approximately ⅓ of the whole and appears at a rate of one out of three amino acids in the amino acid sequence. Glycine is the simplest amino acid. Its position in the molecular chain is less restricted, and glycine makes a significant contribution to the regeneration of the helix structure during gelatinization. It is preferred that imino acids (proline or oxyproline) should be included in large amounts in the amino acids represented by X and Y and account for 10% to 45% of all the amino acids. It is preferred that preferably 80% or more, more preferably 95% or more, most preferably 99% or more of the amino acids in the sequence should be the GXY repeat structures.

In general gelatin, as to the polar amino acids, those having an electric charge and those uncharged are present at a 1:1 ratio. In this context, the polar amino acids specifically refer to cysteine, aspartic acid, glutamic acid, histidine, lysine, asparagine, glutamine, serine, threonine, tyrosine, and arginine. Of them, polar uncharged amino acids refer to cysteine, asparagine, glutamine, serine, threonine, and tyrosine. The ratio of the polar amino acids is 10 to 40%, preferably 20 to 30%, to all amino acids constituting the recombinant gelatin used in the present invention. In addition, it is preferred that the ratio of uncharged amino acids to the polar amino acids should be from 5% to less than 20%, preferably less than 10%. It is further preferred that any one amino acid, preferably two or more amino acids which are selected from serine, threonine, asparagine, tyrosine, and cysteine, should not be contained in the sequence.

In general, minimal ammo acid sequences that function as cell adhesion signals in polypeptides are known (e.g., "Medicina Philosophica", Vol. 9, No. 7 (1990), p. 527, Nagai Shoten Co., Ltd.). It is preferred that the recombinant gelatin used in the present invention should have two or more of these cell adhesion signals in a molecule. Specific sequences are preferably RGD sequences, LDV sequences, REDV sequences, YIGSR sequences, PDSGR sequences, RYVVLPR sequences, LGTIPG sequences, RNIAEIIKDI sequences, IKVAV sequences, LRE sequences, DGEA sequences, and HAV sequences, more preferably RGD sequences, YIGSR sequences, PDSGR sequences, LGTIPG sequences, IKVAV sequences, and HAV sequences, particularly preferably RGD sequences, indicated by single letter codes for amino acids, in terms that many types of cell can adhere thereto. Of the RGD sequences, an ERGD sequence is preferable. The amount of substrates produced by the cells can be improved by using the recombinant gelatin having cell adhesion signals. In the case of, for example, chondrogenic differentiation using mesenchymal stem cells as the cells, the production of glycosaminoglycan (GAG) can be improved.

For the arrangement of the RGD sequences in the recombinant gelatin used in the present invention, it is preferred that the number of amino acids between the RGD sequences should be between 0 and 100, preferably between 25 and 60, and should not be uniformly determined From the viewpoint of cell adhesion/growth, the content of this minimal amino acid sequence is preferably 3 to 50 sequences, more preferably 4 to 30 sequences, particularly preferably 5 to 20 sequences, most preferably 12 sequences, per protein molecule.

In the recombinant gelatin used in the present invention, the ratio of the RGD motifs to the total number of the amino acids is preferably at least 0.4%. In the case where the recombinant gelatin contains 350 or more amino acids, it is preferred that each stretch of 350 amino acids should contain at least one RGD motif. The ratio of the RGD motifs to the total number of the amino acids is more preferably at least 0.6%, further preferably at least 0.8%, further preferably at least 1.0%, further preferably at least 1.2%, most preferably at least 1.5%. The number of the RGD motifs within the recombinant gelatin is preferably at least 4, more preferably 6, further preferably 8, further preferably from 12 to 16, per 250 amino acids. The ratio of the RGD motifs of 0.4% corresponds to at least one RGD sequence per 250 ammo acids. Since the number of the RGD motifs is an integer, gelatin consisting of 251 amino acids must contain at least two RGD sequences in order to satisfy the feature of 0.4%. Preferably, the recombinant gelatin of the present invention contains at least two RGD sequences per 250 amino acids, more preferably at least three RGD sequences per 250 amino acids, further preferably at least four RGD sequences per 250 amino acids. In a further aspect, the recombinant gelatin of the present invention comprises at least 4 RGD motifs, preferably 6, more preferably 8, further preferably 12 to 16 RGD motifs.

Moreover, the recombinant gelatin may be partially hydrolyzed.

It is preferred that the recombinant gelatin used in the present invention should have repeat structures represented by A[(Gly-X-Y)n]mB m is preferably 2 to 10, more preferably 3 to 5. n is preferably 3 to 100, more preferably 15 to 70, most preferably 50 to 65.

It is preferred that a plurality of naturally occurring collagen sequence units should be bonded to repeat units. In this context, the naturally occurring collagen may be any naturally occurring collagen and is preferably type-I, type-II, type-III, type-IV, and type-V collagens, more preferably type-I, type-II, and type-III collagens. In another embodiment, the origin of the collagen is preferably a human, cattle, a pig, a mouse, or a rat, more preferably a human.

The isoelectric point of the recombinant gelatin used in the present invention is preferably 5 to 10, more preferably 6 to 10, further preferably 7 to 9.5.

Preferably, the recombinant gelatin is not deaminated.

Preferably, the recombinant gelatin does not have telopeptide.

Preferably, the recombinant gelatin is a substantially pure collagen material which was prepared from a nucleic acid encoding natural collagen.

The recombinant gelatin used in the present invention is particularly preferably a recombinant gelatin having any of the followings:

(1) the amino acid sequence represented by SEQ ID NO: 1; or (2) an amino acid sequence having 80% or higher (more preferably 90% or higher, most preferably 95% or higher) homology to the amino acid sequence represented by SEQ ID NO: 1 and having biocompatibility.

The recombinant gelatin used in the present invention can be produced by a gene recombination technique known by those skilled in the art and can be produced according to a method described in, for example, EP1014176A2, U.S. Pat. No. 6,992,172, WO2004-85473, or WO2008/103041. Specifically, a gene encoding the amino acid sequence of the predetermined recombinant gelatin is obtained, and this is incorporated in an expression vector to prepare a recombinant expression vector, which is then introduced in appropriate hosts to prepare transformants. The obtained transformants are cultured in an appropriate medium, whereby the recombinant gelatin is produced. Thus, the produced recombinant gelatin can be collected from the cultures to prepare the recombinant gelatin used in the present invention.

(1-4) Polymer Blocks Having Biocompatibility

In the present invention, blocks (mass) comprising the above-described polymer material having biocompatibility are used. A production method for the polymer blocks is not particularly limited. For example, solid matter comprising the polymer can be pulverized using a pulverizer (New Power Mill, etc.) and then sized through a sieve to obtain a block having the desired size.

The size of each polymer block is preferably from 1 µm to 700 µm, more preferably from 10 µm to 700 µm, further preferably from 10 µm to 300 µm, further preferably from 20 lam to 150 µm, particularly preferably from 25 µm to 106 µm. Moreover, the polymer block may be in a long string-like form equal to or longer than 700 µm having a thickness in the size range described above and may be in a sheet or gel form having a thickness in the size range described above. The cells can be more uniformly present in the construct by adopting this preferable range.

(2) Cells

The cells used in the present invention can be selected appropriately depending on the purpose of the cell construct of the present invention. The type thereof is not particularly limited. Moreover, the cells used may be of one type, or a combination of a plurality of types may be used, depending of the usage purpose of the cell construct. Furthermore, the cells used are preferably animal cells, more preferably vertebrate-derived cells, particularly preferably human-derived cells. The type of the vertebrate-derived cells (particularly, human-derived cells) may be any of pluripotent cells, somatic stem cells, precursor cells, and mature cells. For example, ES cells, GS cells, or iPS cells can be used as pluripotent cells. For example, mesenchymal stem cells (MSCs), hematopoietic stem cells, amnion cells, cord blood cells, bone marrow-derived cells, cardiac muscle stem cells, fat-derived stem cells, or neural stem cells can be used as somatic stem cells. For example, cells derived from the skin, dermis, epidermis, muscle, cardiac muscle, nerve, bone, cartilage, endothelium, brain, epithelium, heart, kidney, liver, pancreas, spleen, oral cavity, cornea, bone marrow, cord blood, amnion, or hair can be used as precursor cells and mature cells. For example, ES cells, iPS cells, MSCs, cartilage cells, osteoblasts, osteoprogenitor cells, mesenchyme cells, myoblasts, cardiac muscle cells, cardiac myoblasts, nerve cells, hepatic cells, beta cells, fibroblasts, corneal endothelial cells, vascular endothelial cells, corneal epithelial cells, amnion cells, cord blood cells, bone marrow-derived cells, or hematopoietic stem cells can be used as human-derived cells. Moreover, the origin of the cells may be any of autologous cells and heterologous cells. When a plurality of types of cells are used in combination, an example of such a combination is a combination of vascular cells and other cells. Examples of vascular cells include vascular endothelial cells, vascular endothelial precursor cells, and hematopoietic stem cells. With the use of vascular cells in combination with other cells, blood vessels can be induced to the cell construct of the present invention, and nutrients, oxygen, and other substances can be supplied.

(3) Cell Construct

In the present invention, the polymer blocks having biocompatibility and the cells mentioned above are used to three-dimensionally arrange a plurality of polymer blocks in a mosaic pattern in spaces among a plurality of cells. This enables delivery of nutrients from the outside to the inside of a three-dimensional cell construct, and it leads to the formation of a three-dimensional cell construct with sufficient thickness. At the same time, three-dimensional cell constructs are capable of spontaneously fusing to each other through the actions of cells existing in the outer circumference thereof The thickness or diameter of the cell construct of the present invention can be adjusted to a desired level by the method described hereinbelow. The lower limit is preferably 215 µm, with 400 µm being more preferable, and 730 µm being most preferable. The upper limit for the thickness or diameter is not particularly limited. In general, the upper limit is preferably 3 cm, more preferably 2 cm, and still more preferably 1 cm. The thickness or diameter of the cell construct is preferably between 400 µm and 3 cm, more preferably between 500 µm and 2 cm, and further preferably between 720 µm and 1 cm. In the examples, cell constructs of 720 µm or larger were first prepared (FIG. 3), and a 813-µm-thick cell construct was then prepared via fusion (FIG. 10). The cell construct of the present invention is characterized in that regions comprising polymer blocks and regions comprising cells are arranged in a mosaic pattern. The term "thickness or diameter of the cell construct" used herein is defined as follows. When a given point A in the cell construct is selected, the length of a line segment that splits the cell construct so as to minimize the distance from the outside of the cell construct to point A is designated as "line segment A" among the straight lines passing through point A. A point A that maximizes the length of line segment A in the cell construct is selected and the length of the line segment A is designated as the "thickness or diameter of the cell construct."

The cell construct of the present invention is capable of having a sufficient thickness and comprising cells uniformly distributed therein. Thus, such cell construct can be preferably used for cell transplantation, cell culture, virulence evaluation, or other purposes. When the cell construct of the present invention is used for such purposes, preferably, the thickness or diameter of the cell construct according to the present invention may be in the range mentioned above.

Moreover, in the case of using the cell construct of the present invention as a cell construct before fusion or as a cell construct before addition of second polymer blocks in a method (described later) for producing the cell construct of the present invention, the range of the thickness or diameter of the cell construct is preferably from 10 μm to 1 cm, more preferably from 10 μm to 2000 μm, further preferably from 15 μm to 1500 μm, most preferably from 20 μm to 1300 μm.

In the cell construct of the present invention, the ratio between the cells and the polymer blocks is not particularly limited and is preferably a ratio of the polymer blocks per cell from 0.0000001 μg to 1.0 μg, more preferably from 0.000001 μg to 0.1 μg, further preferably from 0.00001 μg to 0.01 μg, most preferably from 0.00002 μg to 0.006 μg. The cells can be more uniformly present by adopting the range described above. Moreover, the cells can exert effects during use in the application described above by adopting the range described above as the lower limit. Components which are optionally present in the polymer blocks can be supplied to the cells by adopting the range described above as the upper limit. In this context, examples of the components in the polymer blocks include, but not particularly limited to, components contained in a medium described later.

(4) Method for Producing Cell Construct

The cell construct of the present invention can be produced by placing the mass (block(s)) consisting of the polymer material having biocompatibility and the cell(s) in an alternating manner. A production method is not particularly limited and is preferably a method involving forming polymer blocks and then inoculating cells thereto. Specifically, the cell construct of the present invention can be produced by incubating a mixture of the polymer blocks having biocompatibility and a culture solution containing the cells. For example, the cells and the polymer blocks having biocompatibility prepared in advance are arranged in a mosaic pattern in a container or in a liquid retained in a container. Means of this arrangement is preferably use of natural aggregation, free fall, centrifugation, or stirring to promote or control the sequence formation of the mosaic pattern consisting of the cells and the biocompatible matrices.

The container used is preferably a container made of a low cell-adhesive material or a non-cell-adhesive material, more preferably a container made of polystyrene, polypropylene, polyethylene, glass, polycarbonate, or polyethylene terephthalate. It is preferred that the container should have a flat, U-shaped, or V-shaped bottom.

The mosaic-pattern cell construct obtained by the method described above can be produced into a cell construct having the desired size by a method, for example,
(1) fusing separately prepared mosaic-pattern cell masses with each other, or
(2) increasing the volume thereof under a differentiation medium or growth medium.
A method for this fusion or increase in volume is not particularly limited.

For example, in the step of incubating a mixture of the polymer blocks having biocompatibility and a culture solution containing the cells, the medium is replaced by a differentiation medium or growth medium, whereby the volume of the cell construct can be increased. Preferably, in the step of incubating a mixture of the polymer blocks having biocompatibility and a culture solution containing the cells, additional polymer blocks having biocompatibility can be added thereto to produce a cell construct of the desired size in which the cells are uniformly present.

The method involving fusing separately prepared mosaic-pattern cell masses with each other is specifically a method for producing a cell construct which comprises a step of fusion of a plurality of cell constructs that comprise a plurality of polymer blocks having biocompatibility and a plurality of cells wherein 1 or a plurality of polymer blocks are arranged in some or all of a plurality of spaces formed by the plurality of cells.

The preferable ranges of the "polymer blocks (type, size, etc.) having biocompatibility", the "cells", the "spaces between the cells", the "obtained cell construct (size, etc.)", the "ratio between the cells and the polymer blocks", and the like according to the method for producing the cell construct of the present invention are similar to the preferable ranges relating to the cell construct of the present invention described above.

Moreover, the thickness or diameter of each cell construct before the fusion is preferably from 10 μm to 1 cm, and the thickness or diameter after the fusion is preferably from 400 μm to 3 cm. In this context, the thickness or diameter of each cell construct before the fusion is more preferably from 10 μm to 2000 μm, further preferably from 15 μm to 1500 μm, most preferably from 20 μm to 1300 μm, and the range of the thickness or diameter after the fusion is more preferably from 500 μm to 2 cm, further preferably from 720 μm to 1 cm.

The above-described method for producing the cell construct of the desired size by adding thereto additional polymer blocks having biocompatibility is specifically a method for producing a cell construct which comprises a step of further adding a second polymer block to a cell construct that comprises a plurality of first polymer blocks having biocompatibility and a plurality of cells wherein 1 or a plurality of polymer blocks are arranged in some or all of a plurality of spaces formed by the plurality of cells, and incubating the same. In this context, the preferable ranges of the "polymer blocks (type, size, etc.) having biocompatibility", the "cells", the "spaces between the cells", the "obtained cell construct (size, etc.)", the "ratio between the cells and the polymer blocks", and the like are similar to the preferable ranges relating to the cell construct of the present invention described above.

In this context, it is preferred that the cell constructs to be fused should be placed at a spacing from 0 to 50 μm, more preferably from 0 to 20 μm, further preferably from 0 to 5 μm. In the fusion of the cell constructs, the cells or substrates produced by the cells are considered to function as an adhesive by cell growth/spreading, so as to connect the cell constructs. The adhesion between the cell constructs can be facilitated by adopting the range described above.

The size of each first polymer block according to the present invention is preferably from 1 μm to 700 μm, more preferably from 10 μm to 700 μm, further preferably from 10 μm to 300 μm, further preferably from 20 μm to 150 μm, particularly preferably from 25 μm to 106 μm. Moreover, the size of each second polymer block according to the present invention is also preferably from 1 μm to 700 μm, more preferably from 10 μm to 700 μm, further preferably from 10 μm to 300 μm, further preferably from 20 μm to 150 μm, particularly preferably from 25 μm to 106 μm.

The range of the thickness or diameter of the cell construct obtained by the method for producing the cell construct of the present invention is preferably from 400 μm to 3 cm, more preferably from 500 μm to 2 cm, further preferably from 720 μm to 1 cm.

For further adding second polymer blocks to the cell construct and incubating them, it is preferred that the pace at which the second polymer blocks are added should be selected appropriately according to the growth rate of the cells used. Specifically, if the second polymer blocks are added at a fast pace, the cells are moved toward the outer region of the cell construct to reduce uniform cell distribution. If they are added at a slow pace, sites with a high ratio of the cells are formed to reduce uniform cell distribution. Thus, the pace is selected in consideration of the growth rate of the cells used.

The cell construct produced by the method for producing a cell construct of the present invention can have a desired configuration and size, as well as a sufficient thickness. Since cells can be uniformly distributed therein, also, the cell construct can be preferably used for cell transplantation, cell culture, virulence evaluation, or other purposes.

Hereinafter, the present invention will be described more specifically with reference to Examples. However, the present invention is not intended to be limited to Examples.

EXAMPLES

Example 1

Recombinant Gelatin

CBE3 described below was prepared as a recombinant gelatin (described in WO2008-103041).
CBE3
Molecular weight: 51.6 kD
Structure: GAP[(GXY)63]3G
The number of amino acids: 571
The number of RGD sequences: 12
Imino acid content: 33%
Substantially 100% of amino acids are the GXY repeat structures. The amino acid sequence of CBE3 does not contain serine, threonine, asparagine, tyrosine, and cysteine.
CBE3 has an ERGD sequence.
Isoelectric point: 9.34, GRAVY value: −0.682, 1/IOB value: 0.323
Amino acid sequence (SEQ ID NO: 1 in the Sequence Listing) (same as SEQ ID NO: 3 in WO2008/103041 except that X at the end was modified to "P")

GAP(GAPGLQGAPGLQGMPGERGAAGLPGPKGERGDAGPKGADGAPGAP

GLQGMPGERGAAGLPGPKGERGDAGPKGADGAPGKDGVRGLAGPIGPPG

ERGAAGLPGPKGERGDAGPKGADGAPGKDGVRGLAGPIGPPGPAGAPGA

PGLQGMPGERGAAGLPGPKGERGDAGPKGADGAPGKDGVRGLAGPP)3G

Example 2

Preparation of Recombinant Gelatin Micro-Blocks

Amorphous micro-blocks were prepared as matrix blocks using the recombinant gelatins CBE3. 1000 mg of the recombinant gelatins was dissolved in 9448 μL of ultrapure water. After addition of 152 μL of 1 N HCl, 400 μL of 25% glutaraldehyde was added thereto at a final concentration of 1.0% and reacted at 50° C. for 3 hours to prepare a cross-linked gelatin gel. This cross-linked gelatin gel was dipped in 1 L of a 0.2 M glycine solution and shaken at 40° C. for 2 hours. Then, the cross-linked gelatin gel was shake-washed for 1 hour in 5 L of ultrapure water, and the ultrapure water was replaced by fresh one, followed by washing again for 1 hour. This procedure was repeated to complete a total of 6 washing operations. The cross-linked gelatin gel thus washed was frozen at −80° C. for 5 hours and then freeze-dried in a freeze dryer (EYELA, FDU-1000). The obtained freeze-dried product was pulverized with New Power Mill (Osaka Chemical Co., Ltd., New Power Mill PM-2005). The pulverization was performed at the maximum number of revolutions for a total of 5 minutes (1 minute×5 runs). The obtained particles were sized through a stainless sieve to obtain 25 to 53 μm and 53 to 106 μm recombinant gelatin micro-blocks.

Example 3

Preparation of Natural Gelatin Micro-Blocks

Amorphous micro-blocks were prepared as matrix blocks using natural gelatin (Nippi, Inc., Nippi gelatin/high grade gelatin APAT). 1000 mg of the natural gelatin was dissolved in 9448 μL of ultrapure water. After addition of 152 μL of 1 N HCl, 400 μL of 25% glutaraldehyde was added thereto at a final concentration of 1.0% and reacted at 50° C. for 3 hours to prepare a cross-linked gelatin gel. This cross-linked gelatin gel was dipped in 1 L of a 0.2 M glycine solution and shaken at 40° C. for 2 hours. Then, the cross-linked gelatin gel was shake-washed for 1 hour in 5 L of ultrapure water, and the ultrapure water was replaced by fresh one, followed by washing again for 1 hour. This procedure was repeated to complete a total of 6 washing operations. The cross-linked gelatin gel thus washed was frozen at −80° C. for 5 hours and then freeze-dried in a freeze dryer (EYELA, FDU-1000). The obtained freeze-dried product was pulverized with New Power Mill (Osaka Chemical Co., Ltd., New Power Mill PM-2005). The pulverization was performed at the maximum number of revolutions for a total of 5 minutes (1 minute×5 runs). The obtained particles were sized through a stainless sieve to obtain 25 to 53 μm and 53 to 106 μm natural gelatin micro-blocks.

Example 4

Preparation of Mosaic Cell Mass Using Recombinant Gelatin Micro-Blocks

Human bone marrow-derived mesenchymal stem cells (hMSCs) were adjusted to 500000 cells/mL with a growth medium (Takara Bio Inc.; MSCGM-CD™ BulletKit™). After addition of recombinant gelatin micro-blocks prepared in Example 2 to be 1.0 mg/mL, 100 μL of the mixture was inoculated to a Sumilon Celltight X96U plate (Sumitomo Bakelite Co., Ltd., U-shaped bottom) and left standing for 18 hours to prepare a spherical mosaic cell mass of approximately 1 mm in diameter consisting of the recombinant gelatin micro-blocks and the hMSC cells (0.002 μg of the polymer blocks per cell). Then, the medium was replaced by a chondrogenic differentiation medium (Takara Bio Inc.; hMSC Differentiation BulletKit™, Chondrogenic, TGF-β3) (200 μL). At Day 7, a spherical mosaic cell mass of 1.54 mm in diameter (=thickness) was formed (FIG. 1). In this context, this mosaic cell mass was prepared in a spherical shape because of being prepared in the U-shaped plate. Medium replacement was performed at Days 3, 7, 10, 14, 17, and 21.

Example 5

Preparation of Mosaic Cell Mass Using Natural Gelatin Micro-Blocks

Human bone marrow-derived mesenchymal stem cells (hMSCs) were adjusted to 500000 cells/mL with a growth medium (Takara Bio Inc.; MSCGM-CD™ BulletKit™).

After addition of natural gelatin micro-blocks prepared in Example 3 to be 1.0 mg/mL, 100 μL of the mixture was inoculated to a Sumilon Celltight X96U plate and left standing for 18 hours to prepare a spherical mosaic cell mass of approximately 1 mm in diameter consisting of the natural gelatin micro-blocks and the hMSC cells (0.002 μg of the polymer blocks per cell). Then, the medium was replaced by a chondrogenic differentiation medium (Takara Bio Inc.; hMSC Differentiation BulletKit™, Chondrogenic, TGF-β3) (200 μL). At Day 7, a spherical mosaic cell mass of 1.34 mm in diameter (=thickness) was formed (FIG. 2). In this context, this mosaic cell mass was prepared in a spherical shape because of being prepared in the U-shaped plate.

Human bone marrow-derived mesenchymal stem cells (hMSCs) were adjusted to 500000 cells/mL with a growth medium (Takara Bio Inc.; MSCGM-CD™ BulletKit™). The natural gelatin micro-blocks prepared in Example 3 were prepared by changing the conditions to final concentrations of 0.005 mg/mL, 0.01 mg/mL, 0.1 mg/mL, 0.2 mg/mL, 1.0 mg/mL and 2.0 mg/mL, 100 μL of each mixture was inoculated to a Sumilon Celltight X96U plate and left standing for 18 hours to successfully prepare spherical mosaic cell masses of a little less than 1 mm in diameter (0.00001, 0.0002, 0.0004, 0.002, and 0.004 μg of the polymer blocks per cell).

Example 6

Sample Analysis

A tissue slice was prepared for the mosaic cell mass prepared in Example 4 using the recombinant gelatin micro-blocks. After medium removal from the mosaic cell mass in the medium prepared in Example 4, the resulting mosaic cell mass was washed by the addition of 200 μL of PBS, and this PBS was removed. This washing step was repeated twice. Then, the washed mosaic cell mass was dipped in 10% formalin, and formalin fixation was performed for 2 days. Then, the resulting cell mass was embedded in paraffin to prepare a tissue slice. The slice was stained with HE (hematoxylin-eosin), and the states of the cells and the gelatin micro-blocks were analyzed. The results are shown in FIGS. 3, 4, and 5. It could thereby be confirmed that: a three-dimensional construct in which the gelatin micro-blocks and the cells were arranged in a mosaic pattern was prepared; and the cells were present in a normal state in the mosaic cell mass. Moreover, from this cross-sectional slice, it was shown that a mosaic cell mass of at least 720 μm or larger in thickness could be prepared.

Example 7

Fusion of Mosaic Cell Masses

Whether the mosaic cell masses prepared in Example 4 could be fused, i.e., whether the mosaic cell masses arranged were able to form a larger three-dimensional construct by natural fusion, was examined. Two, three, or four mosaic cell masses of the 6th day prepared in Example 4 were arranged in a Sumilon Celltight X96U plate and cultured for 5 days. As a result, it was revealed that the cells placed on the periphery of each mosaic cell mass bound the mosaic cell masses to each other, whereby the mosaic cell masses were naturally fused. FIG. 6 shows a photograph taken with a stereoscopic microscope. Regarding the mosaic cell masses at the fusion start date (referred to as Day 6), the mosaic cell masses were merely placed adjacently to each other. By contrast, at the 5th day from the start of fusion (referred to as Day 11), a new layer was formed between the mosaic cell masses, demonstrating the manner in which the mosaic cell masses were fused. Also, FIGS. 7, 8, 9, 10, and 11 show results of preparing a tissue slice of the fused mosaic cell masses and HE-staining the cross section thereof (fixation was performed using 10% formalin, and embedding was performed using paraffin embedding). As is evident from the drawings, a fusion layer was formed between the mosaic cell masses by the cells and extracellular matrices produced by the cells so as to fuse and bind the mosaic cell masses to each other. It was thereby shown that the mosaic cell masses prepared in the present invention could be naturally fused and were able to form a larger construct by this fusion. Thus, it is demonstrated that use of the present invention achieves both of the preparation of a cell sheet having a thickness and the preparation of a more steric three-dimensional construct.

Example 8

Preparation of Mosaic Cell Mass Under Growth Medium Using Recombinant Gelatin Micro-Blocks Human bone marrow-derived mesenchymal stem cells (hMSCs) were adjusted to 500000 cells/mL with a growth medium (Takara Bio Inc.; MSCGM-CD™ BulletKit™). After addition of recombinant gelatin micro-blocks prepared in Example 2 to be 1.0 mg/mL, 100 μL of the mixture was inoculated to a Sumilon Celltight X96U plate and left standing for 18 hours to prepare a spherical mosaic cell mass of 1 mm in diameter (0.002 μg of the polymer blocks per cell). Then, the volume of the medium was increased to 200 μL, and the mosaic cell mass was cultured with the medium replaced every 3 days. At Day 7, a spherical mosaic cell mass of 1.34 mm in diameter (=thickness) was formed (in this context, this mosaic cell mass was prepared in a spherical shape because of being prepared in the U-shaped plate). A photograph of a slice of the mosaic cell mass of Day 7 is shown in FIGS. 16 and 17. As is evident from the drawings, the thickness of even a site with a small thickness reached at least 624 μm or larger on this cross-sectional slice.

Example 9

Increase in Volume of Mosaic Cell Mass (Under Growth Medium)

0.1 mg of the recombinant gelatin micro-blocks prepared in Example 2 was suspended in a growth medium (Takara Bio Inc.; MSCGM-CD™ BulletKit™) and was added during medium replacement to the mosaic cell mass of the 3rd day (Day 3) prepared in Example 8. Subsequently, 0.1 mg of the recombinant gelatin micro-blocks was added at the time of medium replacement at Days 7, 10, 14, 17, and 21.

Time-dependent change in each of diameter (calculated as an average of two different diameters) in the observation of this mosaic cell mass under stereoscopic microscope, area of the photographed mosaic cell mass, and calculated volume (calculated according to $4/3\pi r^3$ from the diameter determined above) is shown in FIGS. 12, 13, 14, and 15. As a result, a spherical mosaic cell mass of 3.41 mm in average diameter (=thickness) was finally formed at Day 21. It is thereby demonstrated that a mosaic cell mass up to at least 3.41 mm in size can be prepared. It is also demonstrated that the size can be increased by continuing increase in volume by this approach.

A tissue slice (HE-stained) at this time is shown in FIGS. 18 and 19. As is evident from the drawings, the cells and the recombinant gelatin micro-blocks were arranged in a mosaic pattern. Moreover, since the mosaic cell mass was approximately 3 mm in size and small as a sample, it was extremely difficult to correctly create a cross section through the center of the sphere. Thus, although the deepest portion of the sphere was not obtained in the slice, even a portion from which this slice was collected in the sample was shown to be at least 1.17 mm in thickness.

As shown in FIGS. 12, 13, and 14, diameter was not changed in a mosaic cell mass cultured without adding the recombinant gelatin micro-blocks during medium replacement at Days 7, 10, 14, 17, and 21. In the mosaic cell mass cultured without adding the recombinant gelatin micro-blocks, a layered structure consisting only of the cells and extracellular matrices produced by the cells is formed by the proliferated cells in the outermost layer of the mosaic cell mass. As a result, the state in which the diffusion of nutrition is blocked by the layer of the cells and the produced extracellular matrices is formed to prevent the cells from being further proliferated (sized up). This is the reason for no change in diameter. On the other hand, when the recombinant gelatin micro-blocks are constantly added at the timing of medium replacement, these recombinant gelatin micro-blocks are always fit in the mosaic pattern together with the proliferated cells, whereby the mosaic structure consisting of the cells and the recombinant gelatin micro-blocks can continue to be maintained even after cell proliferation. As a result, the supply pathway of nutrition provided by the recombinant gelatin micro-blocks is always secured, and the outer layer unintentionally formed by the cells and the produced extracellular matrices is not generated. The resulting mosaic cell mass can be sized up.

Example 10

Increase in Volume of Mosaic Cell Mass (Under Chondrogenic Differentiation Medium)

0.1 mg of the recombinant gelatin micro-blocks (0.1 mg) prepared in Example 2 was suspended in a chondrogenic differentiation medium (Takara Bio Inc.; hMSC Differentiation BulletKit™, Chondrogenic, TGF-β3) and was added during medium replacement to the mosaic cell mass of the 3rd day (Day 3) prepared in Example 4. Subsequently, 0.1 mg of the recombinant gelatin micro-blocks was added at the time of medium replacement at Days 7, 10, 14, 17, and 21.

Time-dependent change in each of diameter (calculated as an average of two different diameters) in the observation of this mosaic cell mass under stereoscopic microscope, area of the photographed mosaic cell mass, and calculated volume (calculated according to $4/3\pi r^3$ from the diameter determined above) is shown in FIGS. 12, 13, 14, and 15. As a result, a spherical mosaic cell mass of 2.05 mm in average diameter (=thickness) was finally formed at Day 21. It is thereby demonstrated that a mosaic cell mass up to at least 2.05 mm in size can be prepared. It is also demonstrated that the size can be increased by continuing increase in volume by this approach.

A tissue slice (HE-stained) at this time is shown in FIGS. 20 and 21. As is evident from the drawings, the cells and the recombinant gelatin micro-blocks were arranged in a mosaic pattern. Moreover, since the mosaic cell mass was approximately 2 mm in size and small as a sample, it was extremely difficult to correctly create a cross section through the center of the sphere. Thus, although the deepest portion of the sphere was not obtained in the slice, even a portion from which this slice was collected in the sample was shown to be at least 897 μm in thickness.

As shown in FIGS. 12, 13, and 14, diameter was not changed in a mosaic cell mass cultured without adding the recombinant gelatin micro-blocks during medium replacement at Days 7, 10, 14, 17, and 21. In the mosaic cell mass cultured without adding the recombinant gelatin micro-blocks, a layered structure consisting only of the cells and extracellular matrices produced by the cells is formed by the proliferated cells in the outermost layer of the mosaic cell mass. As a result, the state in which the diffusion of nutrition is blocked by the layer of the cells and the produced extracellular matrices is formed to prevent the cells from being further proliferated (sized up). This is the reason for no change in diameter. On the other hand, when the recombinant gelatin micro-blocks are constantly added at the timing of medium replacement, these recombinant gelatin micro-blocks are always fit in the mosaic pattern together with the proliferated cells, whereby the mosaic structure consisting of the cells and the gelatin micro-blocks can continue to be maintained even after cell proliferation. As a result, the supply pathway of nutrition provided by the recombinant gelatin micro-blocks is always secured, and the outer layer unintentionally formed by the cells and the produced extracellular matrices is not generated. The resulting mosaic cell mass can be sized up.

Example 11

Determination of Amount of Gag Produced in Mosaic Cell Mass (Time-Dependent Change)

The amount of glycosaminoglycan in each mosaic cell mass was determined for the mosaic cell masses prepared in Examples 4 and 5 (hMSC cells+recombinant gelatin and hMSC cells+natural gelatin) and a cell mass prepared using only the cells (prepared by the same approach as in Example 4 without the gelatin blocks). Measurement was performed by a method using a Dimetylmethylene blue dye (Farndale et al., Improved quantitation and sulphated glycosaminoglycans by use of dimethylmethylene blue. Biochimica et Biophysica Acta 883 (1986) 173-177), and Sulfated GAG Quantification Kit (Seikagaku Biobusiness Corp.) was used as a reagent. Absorbance at 530 nm was measured for quantification. As shown in FIG. 21, it was confirmed that characteristic absorption peaks were seen at 525-530 nm by the approach.

Results of determining the amount of GAG over time are shown in the graph of FIG. 22. As a result, the amount of glycosaminoglycan (GAG) produced was low in the cell mass prepared without the gelatin micro-blocks, whereas the amount of GAG produced was exceedingly high in the mosaic cell mass prepared with the natural gelatin micro-blocks and the mosaic cell mass prepared with the recombinant gelatin micro-blocks. It could thereby be confirmed that: chondrogenic differentiation was promoted in the mosaic cell masses prepared in Examples 4 and 5; and the prepared mosaic cell masses had functions as cells (had the ability to produce GAG). Furthermore, the amount of GAG produced was significantly higher in the mosaic cell mass prepared with the recombinant gelatin micro-blocks than the mosaic cell mass prepared with the natural gelatin micro-blocks. This demonstrated that the mosaic cell mass prepared with the recombinant gelatin micro-blocks was able to maintain higher cell activity and substrate-producing activity than those brought about by the natural gelatin micro-blocks, and showed that use of the recombinant gelatin was able to achieve the amount of the substrate produced, which was impossible to achieve with the natural gelatin.

Example 12

ATP Quantification for Mosaic Cell Mass

The amount of ATP (adenosine triphosphate) produced/retained by the cells in each mosaic cell mass was determined ATP is known as an energy source for general organisms. The active metabolic state and activity state of cells can be known by determining the amount of ATP synthesized/retained. CellTiter-Glo (Promega Corp.) was used in measurement. For comparison, the amount of ATP in each mosaic cell mass was determined using CellTiter-Glo for the mosaic cell masses prepared in Examples 4 and 5 (hMSC cells+recombinant gelatin and hMSC cells+natural gelatin) and a cell mass prepared using only the cells (prepared by the same approach as in Example 4 without the gelatin blocks), all of which were of Day 7.

The results are shown in FIG. 23. As is thereby evident, the amount of ATP produced/retained was significantly higher (p<0.01) in the mosaic cell mass prepared using the gelatin micro-blocks than the cell mass prepared using only the cells. This suggests that the micro-blocks are fit in the mosaic pattern, whereby the nutrition supply pathway into the mosaic cell mass is provided by the micro-blocks and the highly active metabolic state of the cells is more maintained than in the mass consisting only of the cells. It was further demonstrated that the amount of ATP produced/retained was significantly higher in the mosaic cell mass prepared with the recombinant gelatin micro-blocks than the mosaic cell mass prepared with the natural gelatin micro-blocks. It was thereby demonstrated that the mosaic cell mass prepared with the recombinant gelatin micro-blocks exhibited higher cell survival than that brought about by the natural gelatin micro-blocks and the cells within this mosaic cell mass was alive. Use of the recombinant gelatin was shown to be able to achieve improvement in cell survival, which was impossible to achieve with the natural gelatin.

Example 13

Preparation of PLGA Micro-Blocks 0.3 g of PLGA (poly(lactic-co-glycolic acid); Wako Pure Chemical Industries, Ltd., PLGA7520) was dissolved in dichloromethane (3 mL). The PLGA solution was vacuum dried in a dryer (EYELA, FDU-1000) to obtain a dried product of PLGA. The dried product of PLGA was pulverized with New Power Mill (Osaka Chemical Co., Ltd., New Power Mill PM-2005). The pulverization was performed at the maximum number of revolutions for 10 seconds×20 runs. The obtained particles were sized through a stainless sieve to obtain 25 to 53 µm and 53 to 106 µm PLGA micro-blocks.

PLGA: "1/IOB" value: 0.0552

Example 14

Preparation of Mosaic Cell Mass Using PLGA

Human bone marrow-derived mesenchymal stem cells (hMSCs) were adjusted to 500000 cells/mL with a growth medium (Takara Bio Inc.; MSCGM-CD™ BulletKit™). After addition of the PLGA micro-blocks prepared in Example 13 (prepared by changing the conditions to final concentrations of 0.1 mg/mL, 0.2 mg/mL, 1.0 mg/mL, and 2.0 mg/mL), 100 µL of each mixture was inoculated to a Sumilon Celltight X96U plate and left standing for 18 hours to prepare spherical mosaic cell masses of a little less than 1 mm in diameter (0.0002, 0.0004, 0.002, and 0.004 µg of the polymer blocks per cell). Then, the volume of the medium was increased to 200 µL, and each mosaic cell mass was cultured with the medium replaced every 3 days. In this context, this mosaic cell mass was prepared in a spherical shape because of being prepared in the U-shaped plate. A stereoscopic microscope photograph of the PLGA mosaic cell mass of Day 2 is shown in FIG. 24.

Example 15

Preparation of Agarose Micro-Blocks

Ultrapure water (100 mL) was added to 5 g of agarose powders, and the powders were dissolved by heating using a microwave oven. The obtained 5% agarose solution was bought back to room temperature to obtain solid matter. The solid matter was frozen at −80° C. for 5 hours and then freeze-dried in a freeze dryer (EYELA, FDU-1000) to obtain a freeze-dried product of agarose. The freeze-dried product of agarose was pulverized with New Power Mill (Osaka Chemical Co., Ltd., New Power Mill PM-2005). The pulverization was performed at the maximum number of revolutions for 10 seconds×20 runs. The obtained particles were sized through a stainless sieve to obtain 25 to 53 µm and 53 to 106 µm agarose micro-blocks.

IOB value: 3.18

Example 16

Preparation of Mosaic Cell Mass Using Agarose

Human bone marrow-derived mesenchymal stem cells (hMSCs) were adjusted to 500,000 cells/mL with a growth medium (Takara Bio Inc.; MSCGM-CD™ BulletKit™). After addition of the agarose micro-blocks prepared in Example 15 (prepared by changing the conditions to final concentrations of 0.1 mg/mL and 1.0 mg/mL), 100 µL of each mixture was inoculated to a Sumilon Celltight X96U plate and left standing for 18 hours to prepare spherical mosaic cell masses of a little less than 1 mm in diameter (0.0002 and 0.002 µg of the polymer blocks per cell). Then, the volume of the medium was increased to 200 µL, and each mosaic cell mass was cultured with the medium replaced every 3 days. In this context, this mosaic cell mass was prepared in a spherical shape because of being prepared in the U-shaped plate.

Example 17

Preparation of Mosaic Cell Mass Using Cardiac Muscle Cells

New-born SD rat cardiac muscle cells (rCMCs) were adjusted to 500000 cells/mL with a medium for cardiac muscle cells (Primary Cell Co., Ltd; CMCM culture medium for cardiac muscle cells). After addition of recombinant gelatin micro-blocks prepared in Example 2 to be 0.5, 1.0, or 3.0 mg/mL, 100 µL of each mixture was inoculated to a Sumilon Celltight X96U plate (Sumitomo Bakelite Co., Ltd., U-shaped bottom) and left standing for 18 hours to prepare mosaic cell masses of approximately 1 to 2 mm in diameter consisting of the recombinant gelatin micro-blocks and the rCMC cells (0.001, 0.002, and 0.006 μg of the polymer blocks per cell). Medium replacement was performed at Days 3, 7, 10, 14, 17, and 21.

At the stages of Days 1 and 3, the rCMC mosaic cell mass could already be confirmed to beat in synchronization as the whole construct (FIG. 25). Since moving images are difficult to show in the specification, FIG. 25 is an image taken by capturing still images of the same spot after 0.2 seconds from the moving images. As is evident from the site marked with the triangle, the whole construct moved in two pictures.

This could show that even use of cardiac muscle cells was able to form the three-dimensional cell construct (mosaic cell mass) of the present invention, and also demonstrated that the mosaic cell mass containing the cardiac muscle cells was obtained as a cell construct that beat in synchronization as the whole construct.

Example 18

Preparation of Mosaic Cell Mass Using GFP-Expressing HUVECs (Human Umbilical Vein Endothelial Cells)

GFP-expressing human umbilical vein endothelial cells (GFP-HUVECs; Angio-Proteomie) were adjusted to 500000 cells/mL with a medium for endothelial cells (Kurabo Industries Ltd.; Medium 200S, LSGS, antimicrobial agent GA solution). After addition of recombinant gelatin micro-blocks prepared in Example 2 to be 0.3, 1.0, or 3.0 mg/mL, 100 μL of each mixture was inoculated to a Sumilon Celltight X96U plate (Sumitomo Bakelite Co., Ltd., U-shaped bottom) (0.0006, 0.002, and 0.006 μg of the polymer blocks per cell). Likewise, the cells were also adjusted to 1,500,000 cells/mL, and after addition of recombinant gelatin micro-blocks prepared in Example 2 to be 1.0 mg/mL, 100 μL or 200 μL of the mixture was inoculated to a Sumilon Celltight X96U plate (Sumitomo Bakelite Co., Ltd., U-shaped bottom) and prepared. All of them were separately left standing for 18 hours to prepare mosaic cell masses of approximately 1 to 2 mm in diameter consisting of the recombinant gelatin micro-blocks and the GFP-HUVEC cells. Medium replacement was performed at Days 3, 7, 10, 14, 17, and 21.

Figure 26:
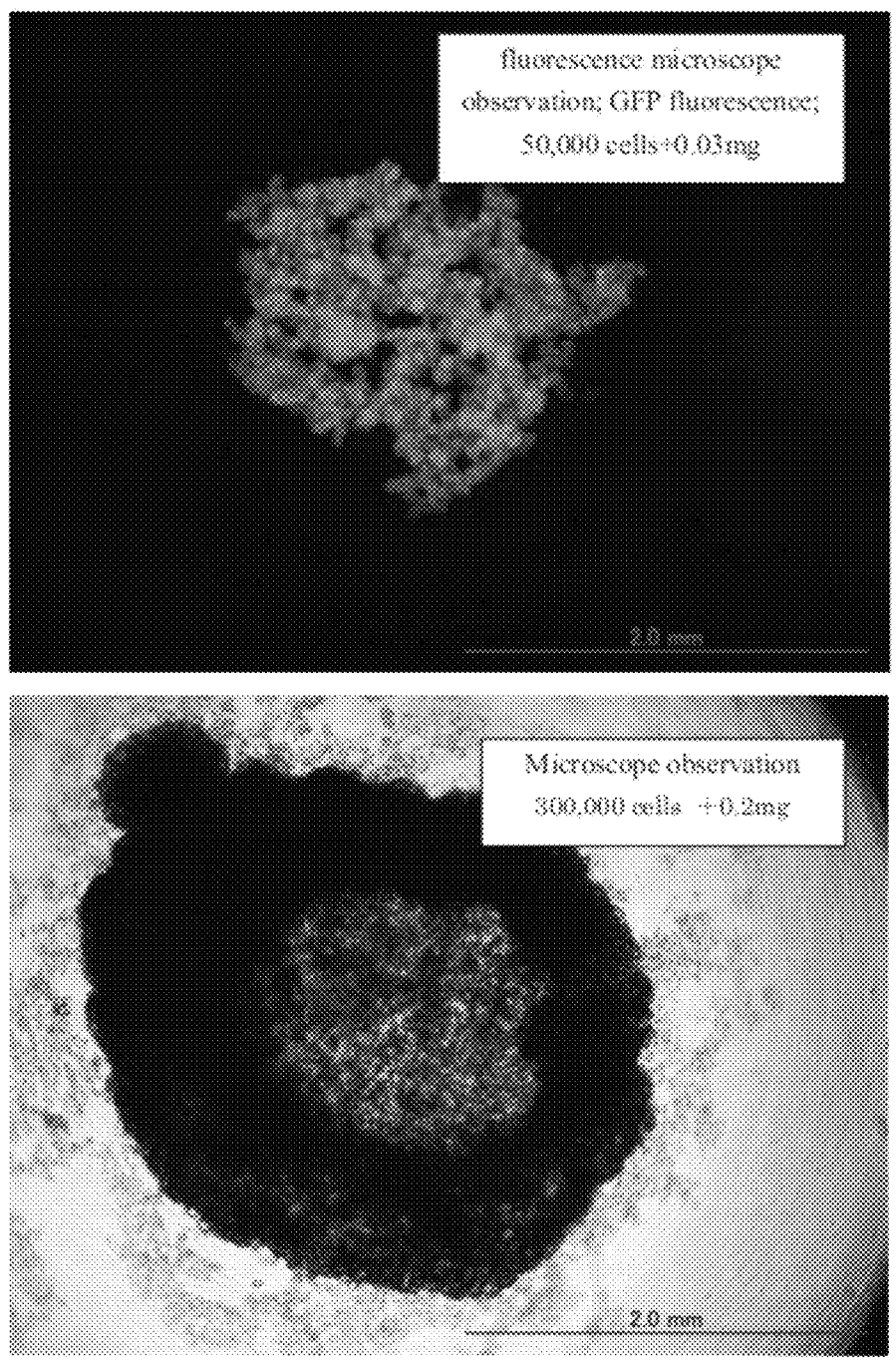
FIG. 26 shows fluorescence microscope photographs and microscope photographs of mosaic cell masses consisting of GFP-expressing HUVEC and the recombinant gelatin micro-blocks (a mosaic cell mass of 50,000 cells+0.03 mg of the micro-blocks, and a mosaic cell mass of 300,000 cells+ 0.2 mg of the micro-blocks).

FIG. 26 shows microscope photographs and fluorescence microscope photographs of a mosaic cell mass of 50000 cells+0.03 mg of the micro-blocks and a mosaic cell mass of 300000 cells+0.2 mg of the micro-blocks. Since the GFP-HUVEC cells emit the fluorescence of GFP, distribution in the mosaic cell mass is easily understood by means of the fluorescence microscope. Even use of vascular endothelial cells was thereby shown to be able to prepare the three-dimensional cell construct (mosaic cell mass) of the present invention.

It was also demonstrated that the cell construct (mosaic cell mass) of the present invention could be formed with diverse cells, such as mesenchymal stem cells, cardiac muscle cells, and vascular endothelial cells. At the same time, it was shown that the cell construct (mosaic cell mass) of the present invention could be formed with diverse polymer blocks, such as recombinant gelatin blocks, animal gelatin blocks, PLGA blocks, and agarose blocks. This proved that the three-dimensional cell construct (mosaic cell mass) of the present invention could be formed with diverse cell species and diverse polymer block species.

The invention claimed is:

1. A cell construct comprising polymer blocks having biocompatibility and cells, wherein the polymer blocks are arranged in spaces between the cells, wherein
   (i) the polymer blocks have surface irregularities and a non-uniform surface shape, and the polymer blocks are obtained by pulverizing freeze-dried product which comprises the polymer,
   (ii) the polymer blocks have a size as defined by a sieve of from 20 μm to 150 μm,
   (iii) the ratio between the polymer blocks and the cells is 0.00001 to 0.006 μg of the polymer blocks per cell; and
   (iv) the thickness or diameter of the cell construct is from 400 μm to 3 cm.

2. The cell construct according to claim 1, wherein the polymer having biocompatibility is polypeptide, polylactic acid, polyglycolic acid, PLGA, hyaluronic acid, glycosaminoglycan, proteoglycan, chondroitin, cellulose, agarose, carboxymethylcellulose, chitin, or chitosan.

3. The cell construct according to claim 1, wherein the polymer having biocompatibility is a recombinant gelatin.

4. The cell construct according to claim 3, wherein the polymer having biocompatibility has two or more cell adhesion signals in one molecule of the polymer.

5. The cell construct according to claim 3, wherein the recombinant gelatin is represented by the formula:

A-[(Gly-X-Y)$_n$]$_m$-B wherein A represents any amino acid or amino acid sequence; B represents any amino acid or amino acid sequence; each X of total n independently represents any amino acid; each Y of total n independently represents any amino acid; n represents an integer of 3 to 100; m represents an integer of 2 to 10; and each Gly-X—Y of total n may be the same as or different from each other.

6. The cell construct according to claim 3, wherein the recombinant gelatin has the amino acid sequence represented by SEQ ID NO: 1.

7. A method for producing a cell construct according to claim 1, which comprises a step of incubating a mixture of polymer blocks having biocompatibility and a cell-containing culture solution.

8. The method according to claim 7, wherein the step of incubating a mixture of polymer blocks having biocompatibility and a cell-containing culture solution comprises exchanging a medium with a differentiation or growth medium.

9. The method according to claim 7, wherein the step of incubating a mixture of polymer blocks having biocompatibility and a cell-containing culture solution further comprises further adding polymer blocks having biocompatibility.

10. A cell construct which is obtained by fusion of a plurality of the cell constructs according to claim 1.

11. A method for producing a cell construct which is obtained by fusion of a plurality of the cell constructs according to claim 1, which comprises a step of subjecting a plurality of the cell constructs according to claim 1 to fusion.

12. The cell construct according to claim 1, wherein the cells are uniformly distributed by three-dimensionally arranging the bio-compatible polymer blocks and cells.

13. the cell construct according to claim 1, wherein the cells are mesenchymal stem cells, cardiac muscle cells or vascular endothelial cells.

* * * * *